United States Patent
Pushpala et al.

(10) Patent No.: US 8,945,592 B2
(45) Date of Patent: Feb. 3, 2015

(54) SUFENTANIL SOLID DOSAGE FORMS COMPRISING OXYGEN SCAVENGERS AND METHODS OF USING THE SAME

(75) Inventors: Shamim Pushpala, Sunnyvale, CA (US); Larry Hamel, Mountain View, CA (US); Stelios Tzannis, Newark, CA (US); Evangeline Cruz, Hayward, CA (US)

(73) Assignee: AcelRx Pharmaceuticals, Inc., Redwood City, CA (US)

( * ) Notice: Subject to any disclaimer, the term of this patent is extended or adjusted under 35 U.S.C. 154(b) by 980 days.

(21) Appl. No.: 12/275,485

(22) Filed: Nov. 21, 2008

(65) Prior Publication Data
US 2010/0130551 A1   May 27, 2010

(51) Int. Cl.
*A61K 9/00*     (2006.01)
*A61K 31/445*   (2006.01)
*A61K 31/4535*  (2006.01)
*A61K 9/20*     (2006.01)

(52) U.S. Cl.
CPC .......... *A61K 31/4535* (2013.01); *A61K 9/2054* (2013.01)
USPC .......................................... 424/400; 514/326

(58) Field of Classification Search
CPC ........... A61K 31/4468; A61K 31/4535; A61K 9/0056; A61K 9/006; A61K 47/10; A61K 9/2054; C07D 401/06
USPC .......................................... 424/400; 514/326
See application file for complete search history.

(56) References Cited

U.S. PATENT DOCUMENTS

| | | | |
|---|---|---|---|
| 2,621,655 A | 12/1952 | Olson et al. |
| 3,444,858 A | 5/1969 | Russell |
| 4,020,558 A | 5/1977 | Cournut et al. |
| 4,226,848 A | 10/1980 | Nagai et al. |
| 4,229,447 A | 10/1980 | Porter et al. |
| 4,237,884 A | 12/1980 | Erikson |
| 4,474,308 A | 10/1984 | Bergeron |
| 4,582,835 A | 4/1986 | Lewis et al. |
| 4,671,953 A | 6/1987 | Stanley et al. |
| 4,764,378 A | 8/1988 | Keith et al. |
| 4,785,969 A | 11/1988 | McLaughlin |
| 4,863,737 A | 9/1989 | Stanley et al. |
| 4,873,076 A | 10/1989 | Fishman et al. |
| 4,880,634 A | 11/1989 | Speiser et al. |
| 4,950,234 A | 8/1990 | Fujioka et al. |
| 5,080,903 A | 1/1992 | Ayache et al. |
| 5,112,616 A | 5/1992 | McCarty et al. |
| 5,122,127 A | 6/1992 | Stanley et al. |
| 5,132,114 A | 7/1992 | Stanley et al. |

(Continued)

FOREIGN PATENT DOCUMENTS

| CN | 2776369 Y | 5/2006 | |
|---|---|---|---|
| EP | 1 243 524 A2 * | 9/2002 | ............. B65D 81/26 |

(Continued)

OTHER PUBLICATIONS

ACTIQ fact sheet printed Mar. 2004.

(Continued)

*Primary Examiner* — Aradhana Sasan
(74) *Attorney, Agent, or Firm* — Cooley LLP (57) ABSTRACT

Compositions and methods effective to minimize or eliminate the presence of oxidative degradation products in solid dosage forms comprising sufentanil are provided.

26 Claims, 2 Drawing Sheets

(56) References Cited

U.S. PATENT DOCUMENTS

| | | |
|---|---|---|
| 5,178,878 A | 1/1993 | Wehling et al. |
| 5,223,264 A | 6/1993 | Wehling et al. |
| 5,236,714 A | 8/1993 | Lee et al. |
| 5,288,497 A | 2/1994 | Stanley et al. |
| 5,288,498 A | 2/1994 | Stanley et al. |
| 5,296,234 A | 3/1994 | Hadaway et al. |
| 5,348,158 A | 9/1994 | Honan et al. |
| 5,352,680 A | 10/1994 | Portoghese et al. |
| 5,482,965 A | 1/1996 | Rajadhyaksha et al. |
| 5,489,025 A | 2/1996 | Romick |
| 5,489,689 A | 2/1996 | Mathew |
| 5,507,277 A | 4/1996 | Rubsamen et al. |
| 5,507,807 A | 4/1996 | Shippert |
| 5,657,748 A | 8/1997 | Braithwaite et al. |
| 5,660,273 A | 8/1997 | Discko, Jr. |
| 5,694,919 A | 12/1997 | Rubsamen et al. |
| 5,710,551 A | 1/1998 | Ridgeway et al. |
| 5,724,957 A | 3/1998 | Rubsamen et al. |
| 5,735,263 A | 4/1998 | Rubsamen et al. |
| 5,752,620 A | 5/1998 | Pearson |
| 5,785,989 A | 7/1998 | Stanley et al. |
| 5,800,832 A | 9/1998 | Tapolsky et al. |
| 5,827,525 A | 10/1998 | Liao et al. |
| 5,850,937 A | 12/1998 | Rauche et al. |
| 5,855,908 A | 1/1999 | Stanley et al. |
| 5,945,651 A | 8/1999 | Chorosinski et al. |
| 5,950,632 A | 9/1999 | Reber et al. |
| 5,954,641 A | 9/1999 | Kehr et al. |
| 5,968,547 A | 10/1999 | Reder et al. |
| 5,981,552 A | 11/1999 | Alam et al. |
| 5,995,938 A | 11/1999 | Whaley et al. |
| 5,997,518 A | 12/1999 | Laibovitz et al. |
| 6,024,981 A | 2/2000 | Khankari et al. |
| 6,039,251 A | 3/2000 | Holowko et al. |
| 6,116,414 A | 9/2000 | Discko, Jr. |
| 6,171,294 B1 | 1/2001 | Southam et al. |
| 6,190,326 B1 | 2/2001 | McKinnon et al. |
| 6,200,604 B1 | 3/2001 | Pather et al. |
| 6,210,699 B1 | 4/2001 | Acharya et al. |
| 6,216,033 B1 | 4/2001 | Southam et al. |
| 6,230,927 B1 | 5/2001 | Schoonen et al. |
| 6,234,343 B1 | 5/2001 | Papp et al. |
| 6,248,789 B1 | 6/2001 | Weg et al. |
| 6,264,981 B1 | 7/2001 | Zhang et al. |
| 6,284,512 B1 | 9/2001 | Jones et al. |
| 6,294,999 B1 | 9/2001 | Yarin et al. |
| 6,310,072 B1 | 10/2001 | Smith et al. |
| 6,319,510 B1 | 11/2001 | Yates et al. |
| 6,328,159 B1 | 12/2001 | Discko, Jr. |
| 6,350,470 B1 | 2/2002 | Pather et al. |
| 6,358,944 B1 | 3/2002 | Lederman et al. |
| 6,391,335 B1 | 5/2002 | Pather et al. |
| 6,417,184 B1 | 7/2002 | Ockert et al. |
| 6,425,892 B2 | 7/2002 | Southam et al. |
| 6,484,718 B1 | 11/2002 | Schaeffer et al. |
| 6,488,953 B2 | 12/2002 | Halliday et al. |
| 6,495,120 B2 | 12/2002 | McCoy et al. |
| 6,500,456 B1 | 12/2002 | Capella et al. |
| 6,509,036 B2 | 1/2003 | Pather et al. |
| 6,541,021 B1 | 4/2003 | Johnson et al. |
| 6,576,250 B1 | 6/2003 | Pather et al. |
| 6,599,529 B1 | 7/2003 | Skinhøj et al. |
| 6,605,060 B1 | 8/2003 | O'Neil et al. |
| 6,607,750 B2 | 8/2003 | Upadhyay et al. |
| 6,641,838 B2 | 11/2003 | Pather et al. |
| 6,642,258 B1 | 11/2003 | Bourrie et al. |
| 6,645,528 B1 | 11/2003 | Straub et al. |
| 6,651,651 B1 | 11/2003 | Bonney et al. |
| 6,660,295 B2 | 12/2003 | Watanabe et al. |
| 6,680,071 B1 | 1/2004 | Johnson et al. |
| 6,682,716 B2 | 1/2004 | Hodges et al. |
| 6,685,951 B2 | 2/2004 | Cutler et al. |
| 6,689,373 B2 | 2/2004 | Johnson et al. |
| 6,726,053 B1 | 4/2004 | Harrold |
| 6,752,145 B1 | 6/2004 | Bonney et al. |
| 6,759,059 B1 | 7/2004 | Pettersson et al. |
| 6,761,910 B1 | 7/2004 | Pettersson et al. |
| 6,762,684 B1 | 7/2004 | Camhi et al. |
| 6,764,696 B2 | 7/2004 | Pather et al. |
| 6,776,978 B2 | 8/2004 | Rabinowitz et al. |
| 6,793,075 B1 | 9/2004 | Jeter et al. |
| 6,796,429 B2 | 9/2004 | Cameron et al. |
| 6,824,512 B2 | 11/2004 | Warkentin et al. |
| 6,835,194 B2 | 12/2004 | Johnson et al. |
| 6,855,310 B2 | 2/2005 | Rabinowitz et al. |
| 6,881,208 B1 | 4/2005 | Phipps et al. |
| 6,914,668 B2 | 7/2005 | Brestel et al. |
| 6,916,485 B2 | 7/2005 | Aiache et al. |
| 6,932,983 B1 | 8/2005 | Straub et al. |
| 6,959,808 B2 | 11/2005 | Discko et al. |
| 6,961,541 B2 | 11/2005 | Overy et al. |
| 6,963,289 B2 | 11/2005 | Aljadeff et al. |
| 6,969,508 B2 | 11/2005 | Dugger et al. |
| 6,974,590 B2 | 12/2005 | Pather et al. |
| 6,999,028 B2 | 2/2006 | Egbert et al. |
| 7,018,370 B2 | 3/2006 | Southam et al. |
| 7,018,619 B2 | 3/2006 | Rabinowitz et al. |
| 7,044,125 B2 | 5/2006 | Vedrine et al. |
| 7,044,302 B2 | 5/2006 | Conley et al. |
| 7,070,762 B2 | 7/2006 | Rabinowitz et al. |
| 7,070,764 B2 | 7/2006 | Rabinowitz et al. |
| 7,070,765 B2 | 7/2006 | Rabinowitz et al. |
| 7,072,738 B2 | 7/2006 | Bonney et al. |
| 7,074,935 B2 | 7/2006 | Mathew et al. |
| 7,078,018 B2 | 7/2006 | Rabinowitz et al. |
| 7,078,019 B2 | 7/2006 | Rabinowitz et al. |
| 7,078,218 B2 | 7/2006 | Smith et al. |
| 7,090,830 B2 | 8/2006 | Hale |
| 7,090,866 B2 | 8/2006 | Johnson et al. |
| 7,119,690 B2 | 10/2006 | Lerch et al. |
| 7,168,626 B2 | 1/2007 | Lerch et al. |
| 7,169,378 B2 | 1/2007 | Rabinowitz et al. |
| 7,198,172 B2 | 4/2007 | Hale et al. |
| 7,208,604 B2 | 4/2007 | Mathew et al. |
| 7,215,295 B2 | 5/2007 | Egbert et al. |
| 7,248,165 B2 | 7/2007 | Collins et al. |
| 7,276,246 B2 | 10/2007 | Zhang et al. |
| 7,295,890 B2 | 11/2007 | Jean-Pierre et al. |
| 7,306,812 B2 | 12/2007 | Zhang et al. |
| 7,458,374 B2 | 12/2008 | Hale et al. |
| 7,468,179 B2 | 12/2008 | Rabinowitz et al. |
| 7,484,642 B2 | 2/2009 | Bonney et al. |
| 7,500,444 B2 | 3/2009 | Bonney et al. |
| 7,552,728 B2 | 6/2009 | Bonney et al. |
| 8,202,535 B2 | 6/2012 | Palmer et al. |
| 2001/0020147 A1 | 9/2001 | Staniforth et al. |
| 2002/0026330 A1 | 2/2002 | Klein et al. |
| 2002/0037491 A1 | 3/2002 | Halliday et al. |
| 2002/0071857 A1 | 6/2002 | Kararli et al. |
| 2002/0110578 A1 | 8/2002 | Pather et al. |
| 2002/0142050 A1 | 10/2002 | Straub et al. |
| 2002/0160043 A1 | 10/2002 | Coleman et al. |
| 2003/0008005 A1 | 1/2003 | Cutler et al. |
| 2003/0015196 A1 | 1/2003 | Hodges et al. |
| 2003/0015197 A1 | 1/2003 | Hale et al. |
| 2003/0017175 A1 | 1/2003 | Cutler et al. |
| 2003/0017994 A1 | 1/2003 | Cutler et al. |
| 2003/0022910 A1 | 1/2003 | Cutler et al. |
| 2003/0035776 A1 | 2/2003 | Hodges et al. |
| 2003/0052135 A1 | 3/2003 | Conley et al. |
| 2003/0052787 A1 | 3/2003 | Zerhusen et al. |
| 2003/0077300 A1 | 4/2003 | Wermeling et al. |
| 2003/0088236 A1 | 5/2003 | Johnson et al. |
| 2003/0091629 A1 | 5/2003 | Pather et al. |
| 2003/0099158 A1 | 5/2003 | De la Huerga |
| 2003/0124185 A1 | 7/2003 | Oshlack et al. |
| 2003/0130314 A1 | 7/2003 | Druzgala et al. |
| 2003/0132239 A1 | 7/2003 | Konig et al. |
| 2003/0171401 A1 | 9/2003 | Johnson et al. |
| 2003/0173408 A1 | 9/2003 | Mosher et al. |
| 2003/0181501 A1 | 9/2003 | Le et al. |
| 2003/0185872 A1 | 10/2003 | Kochinke et al. |
| 2003/0190290 A1 | 10/2003 | Ross et al. |
| 2003/0232080 A1 | 12/2003 | Pather et al. |

(56) References Cited

U.S. PATENT DOCUMENTS

| | | |
|---|---|---|
| 2004/0017567 A1 | 1/2004 | Loicht et al. |
| 2004/0025871 A1 | 2/2004 | Davies |
| 2004/0034059 A1 | 2/2004 | Grarup et al. |
| 2004/0037882 A1 | 2/2004 | Johnson et al. |
| 2004/0080515 A1 | 4/2004 | Hagiwara et al. |
| 2004/0092531 A1 | 5/2004 | Chizh et al. |
| 2004/0094564 A1 | 5/2004 | Papp et al. |
| 2004/0096402 A1 | 5/2004 | Hodges et al. |
| 2004/0120896 A1 | 6/2004 | Dugger et al. |
| 2004/0133305 A1 | 7/2004 | Jean Pierre |
| 2004/0157884 A1 | 8/2004 | Johnson et al. |
| 2004/0158349 A1 | 8/2004 | Bonney et al. |
| 2004/0170567 A1 | 9/2004 | Sackler et al. |
| 2004/0180080 A1 | 9/2004 | Furusawa et al. |
| 2004/0185003 A1 | 9/2004 | Rabinowitz et al. |
| 2004/0191178 A1 | 9/2004 | Cutler et al. |
| 2004/0202617 A1 | 10/2004 | Rabinowitz et al. |
| 2004/0213855 A1 | 10/2004 | Pettersson et al. |
| 2004/0248964 A1 | 12/2004 | Crooks et al. |
| 2004/0253307 A1 | 12/2004 | Hague et al. |
| 2005/0038062 A1 | 2/2005 | Burns et al. |
| 2005/0049464 A1 | 3/2005 | Lassers et al. |
| 2005/0054942 A1 | 3/2005 | Melker |
| 2005/0064030 A1 | 3/2005 | Pather et al. |
| 2005/0065175 A1 | 3/2005 | Gonzales et al. |
| 2005/0075273 A1 | 4/2005 | Rabinowitz et al. |
| 2005/0089479 A1 | 4/2005 | Rabinowitz et al. |
| 2005/0101936 A1 | 5/2005 | Gonzales et al. |
| 2005/0122219 A1 | 6/2005 | Petersen et al. |
| 2005/0129737 A1 | 6/2005 | Johnson et al. |
| 2005/0131337 A1 | 6/2005 | Phipps et al. |
| 2005/0142197 A1 | 6/2005 | Moe et al. |
| 2005/0142198 A1 | 6/2005 | Moe et al. |
| 2005/0150488 A1 | 7/2005 | Dave et al. |
| 2005/0150489 A1 | 7/2005 | Dunfield et al. |
| 2005/0163838 A1 | 7/2005 | Moe et al. |
| 2005/0169989 A1 | 8/2005 | Agarwal et al. |
| 2005/0171464 A1 | 8/2005 | Phipps et al. |
| 2005/0176790 A1 | 8/2005 | Bartholomaus |
| 2005/0177275 A1 | 8/2005 | Harvey et al. |
| 2005/0192218 A1 | 9/2005 | Ellis et al. |
| 2005/0258066 A1 | 11/2005 | Conley et al. |
| 2006/0026035 A1 | 2/2006 | Younkes et al. |
| 2006/0031099 A1 | 2/2006 | Vitello et al. |
| 2006/0039959 A1 | 2/2006 | Wessling et al. |
| 2006/0045865 A1 | 3/2006 | Jacob et al. |
| 2006/0062812 A1 | 3/2006 | Ross et al. |
| 2006/0067978 A1 | 3/2006 | Heiler et al. |
| 2006/0069344 A1 | 3/2006 | Southam et al. |
| 2006/0089858 A1 | 4/2006 | Ling et al. |
| 2006/0134200 A1 | 6/2006 | Vandoni et al. |
| 2006/0210632 A1 | 9/2006 | Oury et al. |
| 2006/0216352 A1 | 9/2006 | Nystrom et al. |
| 2006/0229570 A1 | 10/2006 | Lovell et al. |
| 2006/0233718 A1 | 10/2006 | Rabinowitz et al. |
| 2006/0251587 A1 | 11/2006 | Rabinowitz et al. |
| 2006/0292219 A1 | 12/2006 | Pather et al. |
| 2007/0020186 A1 | 1/2007 | Stroppolo et al. |
| 2007/0031502 A1 | 2/2007 | Pettersson et al. |
| 2007/0036853 A1 | 2/2007 | Agarwal et al. |
| 2007/0071806 A1 | 3/2007 | McCarty et al. |
| 2007/0074722 A1 | 4/2007 | Giroux et al. |
| 2007/0104763 A1 | 5/2007 | Jobdevairakkam et al. |
| 2007/0178052 A1 | 8/2007 | Rabinowitz et al. |
| 2007/0184096 A1 | 8/2007 | Ameri et al. |
| 2007/0185084 A1 | 8/2007 | McKinney et al. |
| 2007/0186923 A1 | 8/2007 | Poutiatine et al. |
| 2007/0190130 A1 | 8/2007 | Mark et al. |
| 2007/0207207 A1 | 9/2007 | Tzannis et al. |
| 2007/0260491 A1 | 11/2007 | Palmer et al. |
| 2007/0286900 A1 | 12/2007 | Herry |
| 2007/0299687 A1 | 12/2007 | Palmer et al. |
| 2008/0147044 A1 | 6/2008 | Palmer et al. |
| 2008/0164275 A1 | 7/2008 | Poutiatine et al. |
| 2008/0166404 A1 | 7/2008 | Tzannis et al. |
| 2008/0203107 A1 | 8/2008 | Conley et al. |
| 2008/0268023 A1 | 10/2008 | Palmer et al. |
| 2009/0010992 A1 | 1/2009 | Palmer et al. |
| 2009/0048237 A1 | 2/2009 | Palmer et al. |
| 2009/0131479 A1 | 5/2009 | Palmer et al. |
| 2010/0105735 A1 | 4/2010 | Palmer et al. |
| 2010/0137836 A1 | 6/2010 | Palmer et al. |
| 2010/0253476 A1 | 10/2010 | Poutiatine et al. |
| 2010/0256190 A1 | 10/2010 | Palmer et al. |
| 2011/0091544 A1 | 4/2011 | Palmer |
| 2011/0288128 A1 | 11/2011 | Palmer et al. |
| 2012/0035216 A1 | 2/2012 | Palmer et al. |

FOREIGN PATENT DOCUMENTS

| | | | |
|---|---|---|---|
| EP | 2114383 | 7/2010 | |
| GB | 2309966 | 8/1997 | |
| JP | 2003-525081 A | 8/2003 | |
| JP | 2004-511310 A | 4/2004 | |
| JP | 2004-531806 A | 10/2004 | |
| JP | 2005-199066 A | 7/2005 | |
| WO | 0016750 | 3/2000 | |
| WO | 0057858 | 10/2000 | |
| WO | 0130288 | 5/2001 | |
| WO | WO 01/64182 A2 | 9/2001 | |
| WO | 0197780 | 12/2001 | |
| WO | WO 02/32487 A1 | 4/2002 | |
| WO | WO 02/067903 A2 | 9/2002 | |
| WO | WO 02/067916 A2 | 9/2002 | |
| WO | WO 02/078594 A2 | 10/2002 | |
| WO | 2004069198 | 8/2004 | |
| WO | 2004080515 | 9/2004 | |
| WO | 2005032556 | 4/2005 | |
| WO | 2006097361 | 9/2006 | |
| WO | 2006103418 | 10/2006 | |
| WO | WO 2007 081949 A2 * | 7/2007 | ............ A61M 11/00 |
| WO | WO 2008/085764 A1 | 7/2008 | |
| WO | WO 2008 085765 A2 * | 7/2008 | ............... A61K 9/70 |
| WO | WO 2009/021106 A1 | 2/2009 | |

OTHER PUBLICATIONS

Berthold, et al., (2007) Oral Surg Oral med Oral Pathol Oral Radiol Endo, 84(2):119-24.
Bethune-Volters A, (2006) Anti-cancer drugs, vol. 17, No. 2, pp. 217-224.
Brendenberg, et al., 2003, Acta Universitatis Upsaliensis; Jan. 1983, Comprehensive Summaries of Uppsala Dissertations from the Faculty of Pharmacy 287.
Brendenberg, et al., 2003, European Journal of Pharmaceutical Sciences; 327-334.
Chauvin, Anesth Analg; 1989; 68(1): 1-4.
Coluzzi, et al., 1998, J Pain Symp Manage, 16(3):184-92.
Dale, et al., 2002, Acta Anaesth Scand, 46:759-770.
Darwish et al., 2007, J Clin Pharm 47: 56-63.
Darwish, et al., 2008, Clin Drug Invest, 28(1):1-7.
Darwish, et al., 2007, Expert Opin Pharmacother, 8(13):2011-6.
Darwish, et al., 2006, Clinical Pharmacokinetics, 45(8):843-50.
Darwish, et al., 2006, Clinical Therapies, 28(5):707-14.
Darwish, et al., 2006, Clinical Therapies, 28(5):715-24.
Darwish, et al., 2005, Clinical Pharmacokinetics, 44(12): 1279-86.
Demeules, et al., Eur J Anaesthesiol Suppl. 2003; 28:7-11.
Durfee, et al., 2006, American Journal Drug Delivery, 4(1):1-5(5).
Egan, et al., 2000, Anesthesiology, 92:665-73.
Farnsworth, et al., 1998, Anesth Analg, 86:138-40.
Fentora Package Insert, 100-800mcg dose of fentanyl; buccal absorption with approximately 50% absorbed transmucosally remainder swallowed/absorbed via GI tract. (p. 4 of package insert), 2006.
Gardner-Nix, et al., 2001, J Pain Symptom Manage, 22:627-630.
Geldner, et al., 1997, Paediatric Anaesthesia, 7:103-109.
Gerak, et al., 1998, Psychopharmacology, 137(2):164-74.
Good, et al., 2009, Palliative Medicine, 23:54-58.
Gordon, et al., 2006, Noncol Nurs Forum, 33(2):257-64.
Gram-Hansen, et al., 1988, Int J Clin Pharmacol Ther Toxicol, 26(6):323-4.
Mathieu, et al., 2006, Can J Anaesth, 53:60-66.

(56) References Cited

OTHER PUBLICATIONS

Haynes, et al., 1993, Can J Anaesth, 40(3):286-288.
Helmers, et al., 1989, Can J Anaesth, 36(5):494-497.
Henderson, et al., 1988, Anesthesiology, 68:671-675.
Jackson, et al., 2002, Journal of Pain and Sympt Management, 23(6):450-452.
Jackson, et al., 2006, Journal Clinical Psychopharmacology, 26(1):4-8.
James, et al., 2005, Clinical Radiology, 60:394-396.
Jeannet, et al., 1999, Eur J Paediatric Neurology, 3:73-77.
Joshi, et al., 1993, Indian Pediatr, 30(1):84-5.
Kaplan, et al., 1998, J Clin Pharmacol, 38(1): 14-21.
Karl, et al., 1997, Journal of Clinical Psychopharmacology, 17(3):169-172.
Karl, et al., 1992, Anesthesiology, 76:209-215.
Karl, et al., 1993, Anesthesiology, 78(5):885-91.
KGH Drug Information Bulletin, vol. 37(4) 2, 2004.
Khalil, et al., 1998, Paediatric Anaesthesia, (8):461-465.
Kogan, et al., 2002, Paediatric Anaesthesia, 12:685-689.
Kontinen, et al, 1993, Canadian Journal of Anesthesia, vol. 40, 829-834.
Kroboth, et al, 1995, J Clin Psychopharmacol, 15(4):259-62.
Kunz, et al., 1993, Journal of Pain and Sympt Management, 8(4):189-190.
Lennernas, et al., 2004, Br J Clin Pharmacol, 59(2):249-253.
Lichtor, et al., 1999, Anesth Anal, 89(3):732-8.
Lim, et al., 1997, Can J Anaesth, 44(7):723-6.
Lipworth, et al., 1989, Eur J Clin Pharmacol, 37:567-571.
McCann, et al., 2001, Anesthesia & Analgesia, 93:98-105.
Mendelson J, et al.; J Clin Pharmacol; 1997; 37:31-7.
Monk, et al., 1988, Drugs, 36:286-313.
Motwani JG, Lipworth BJ; Clin Pharmacokinet; 1991; 21(2):83-94.
Mystakidou K, et al.; Drug Deliv. 2006; 13(4):269-76.
Nath RP, et al.; J Clin Pharmacol; 1999; 39:619-23.
Naguib et al., 2000, Anesth Analg, 91:473-9.
Odou, et al., 1999, Eur J Drug Metab Pharmacokinet, 24(1):1-7.
Odou, et al., 1998, Eur J Drug Metab Pharmacokinet, 23(2):87-91.
Okayama, et al., 1984, Eur J Clin Pharamcol, 26:151-155.
Pavlin, et al., Anesthesiology. Jan. 1996; 84(1):23-37.
Portenoy RK, et al.; Pain; 1999; 79:303-12.
Raza, et al., Can J Anaesth. Nov. 1989; 36(6):617-23.
Reisfield G, Wilson G; Journal of Palliative Medicine; 2007; 10(2):465-475.
Reynolds, et al., 2004, Pain, 110:182-188.
Roy et al, Pharm Res; 1990; 7:842-847.
Roy, SD and Flynn, GL; Pharm Research; 1989; 6(2): 147-151.
Scavone, et al., 1987, J Clin Psychpharmacol, 7(5):332-4.
Scavone, et al., 1992, Eur J Clin Pharmacol, 42(4):439-43.
Scavone, et al., 1986, J Clin Pharmacol, 26:208-10.
Scholz J, et al.; Clin Pharmacokin ; 1996; 31:275-292.
Schreiber, et al., 2006, The American Journal of Emergency Medicine, 24:397-401.
Schwagmeier, et al., 1998, Br J Clin Pharmacol, 46:203-69.
Sinatra, et al., 1996, Journal of Clinical Anesthesia, 8:123-129.
Stopperich, et al., 1993, Anesth Prog, 40(4):117-21.
Streisand JB, et al.; Anesthesiology; 1991; 75:223-9.
Streisand JB, et al.; Anesthesiology; 1998; 88:305-9.
Sufenta Package Insert, 2006.
Tweedy, et al., 2001, J Clin Psychpharmacol, 21(3):268-72.
Vercauteren, et al., 1988, Anaesthesia, 43:270-273.
Viitanen, et al., 1999, Can J Anesth, 46(8):766-771.
Walder, et al., Swiss Med Wkly. Jun. 12, 2004; 134(23-24):333-46.
Weinberg, et al., 1988, Clin Pharmacol Ther., 44(3):335-42.
Wheeler, et al., 2002, Paediatric Anesthesia, 12:594-599.
Willens, et al., 1993, Heart and Lung, 22:239-251.
Yager, et al., 1988, Am J Dis Child, 142:931-2.
Yeomans, et al., 2001, Vancouver Hospital and Health Science Center Drug and Therapeutics Newsletter, vol. 8(1) 2.
Zedie, et al., 1996, Clin Pharmacol Ther, 59:341-8.
Zhang, et al., 2002, Clinical Pharmacokinetics, 41(9):661-680.

Office Action for U.S. Appl. No. 11/429,904, mailed Sep. 17, 2008.
Office Action for U.S. Appl. No. 11/980,216, mailed Dec. 24, 2008.
Office Action for U.S. Appl. No. 11/650,230, mailed Sep. 25, 2008.
Office Action for U.S. Appl. No. 11/650,230, Mar. 10, 2009.
Office Action for U.S. Appl. No. 11/429,904, mailed Mar. 5, 2009.
Office Action for U.S. Appl. No. 11/650,227, mailed Dec. 9, 2008.
Office Action for U.S. Appl. No. 11/473,551, mailed Mar. 16, 2009.
Office Action for U.S. Appl. No. 11/473,551, mailed Sep. 26, 2008.
Office Action for U.S. Appl. No. 11/650,227, mailed Jul. 6, 2009.
Office Action for U.S. Appl. No. 11/980,216, mailed Jul. 20, 2009.
ISR WO2008/085764, Date mailed Jun. 23, 2008.
Abrams R, et al., Anesth Prog. 1993;40(3):63-6.
AHFS Drug Information, 28:08.08, 2157-2160, 2007.
Anlar S et al., Pharm Res, 11(2):231-6, 1994.
Bayrak F., et al., J Opiod Management, 3(2):74-78, 2007.
Bovill GJ, et al., Anesthesiology, 61:502-506, 1984.
Brusset A, et al. Clin Drug Invest, 18(5):377-89, 1999.
De Castro J, et al., Acta Anesth Belgica, 107-128, 1976.
de Vries M et al., Critical Reviews in Therapeutic Drug Carrier Systems, 8(3):271-303, 1991.
Ellmauer S, Anesth, 43(3):143-158, 1994.
Enting H. R, et al., J. Pain and Symptom Management, 29(2):213-217, 2005.
Guay J, Can J Anaesth, 39(1): 14-20, 1992.
Halliburton JR, Anesthesiology, 56(3): 229-233, 1988.
Hazardous Substances Data Bank (HSDB); (http://toxnet.nlm.nih.gov) Apr. 9, 2007; Name: Sufentanil; RN: 56030-54-7.
Helmers JH, et al., Eur J Anesth, 11(3):181-5, 1994.
Heshmati et al., Iran. J. Pharmacol. Therap., 5:131-133, 2006.
Ikinci G, et al., Int. J. Pharm, 277(1-2):173-8, 2004.
Kress, Clin. Therap., 31(6) 1177-1191, 2009.
Lehman K. A., et al., Acta Anaesthesiol Scand., 35:221-226, 1991.
Lehman K. A., et al., Acta Anaesthesiol Scand., 37:176-80, 1993.
Mather, Clin. Pharmacokinetics, 8: 422-446, 1983.
Molander L and Lunell E, Eur J Clin Pharmacol, 56(11):813-819, 2001.
Onsolis Package Insert Jul. 2009.
Portenoy RK, et al., Pain, 22(9):805-811, 2006.
Puig MM, et al., Int'l J Clin Pharmaco Ther and Toxicol, 27(5):229-34, 1989.
Rosow CE, Pharmacotherapy, 4:11-19, 1984.
Savoia G, et al., Minerva Anesth, 67(9 Suppl 1):206-16, 2001.
Siepmann et al., Int J Pharm., 25; 201(2):151-64, 2000.
Smith R.B, et al., J Clin Pharmacol., 26(2):120-4, 1986.
Van de Walle J, et al., Acta Anaesth Belg, 27(3):129-38, 2009.
Office Action for U.S. Appl. No. 11/650,174, mailed Oct. 13, 2010.
Office Action for U.S. Appl. No. 11/650,227, mailed Aug. 5, 2010.
Office Action for U.S. Appl. No. 11/825,251, mailed Aug. 5, 2010.
Office Action for U.S. Appl. No. 11/825,212, mailed Mar. 24, 2010.
Office Action for U.S. Appl. No. 11/825,212, mailed Aug. 31, 2010.
Office Action for U.S. Appl. No. 11/980,216, mailed Jan. 5, 2010.
Office Action for U.S. Appl. No. 11/980,216, mailed Jul. 2, 2010.
Office Action for U.S. Appl. No. 11/974,092, mailed Mar. 31, 2010.
Office Action for U.S. Appl. No. 12/187,937, mailed Sep. 16, 2010.
ISR WO2010/059504 mailed Mar. 17, 2010.
ISR WO2010/107761 mailed Jun. 21, 2010.
Office Action for U.S. Appl. No. 11/650,230, mailed Feb. 2, 2010.
Office Action for U.S. Appl. No. 11/650,230, mailed Jun. 16, 2010.
Good P, et al., Palliat Med., 23(1):54-58, 2009.
ISR PCT/US08/72445 WO 2009/021106, mailed Oct. 20, 2008.
ISR WO2007/133478, mailed Aug. 5, 2008.
ISR WO2008/002358, mailed Aug. 21, 2008.
ISR WO2007/081947, mailed Dec. 17, 2007.
ISR WO2007/081948, mailed Feb. 4, 2008.
ISR WO2007/081949, mailed Sep. 11, 2007.
ISR WO2008/085765, mailed Oct. 15, 2008.
Office Action for U.S. Appl. No. 11/825,251, mailed Sep. 21, 2009.
Office Action for U.S. Appl. No. 11/650,230, mailed Aug. 4, 2009.
Office Action for U.S. Appl. No. 11/974,092, mailed Sep. 30, 2009.
Office Action for U.S. Appl. No. 11/473,551, mailed Sep. 11, 2009.
Office Action for U.S. Appl. No. 11/429,904, mailed Aug. 20, 2009.
Restriction Requirement for U.S. Appl. No. 11/825,212, mailed Dec. 9, 2009.

(56) References Cited

OTHER PUBLICATIONS

Office Action for U.S. Appl. No. 11/825,251, mailed Dec. 15, 2009.
Office Action for U.S. Appl. No. 11/650,227, mailed Dec. 15, 2009.
"FDA Guidance for Industry: Container Closure Systems for Packaging Human Drugs and Biologics," May 1999, pp. 1-E2.
"Triazolam" Drug Facts and Comparisons (Fiftieth Edition). 1996. Wolters Kluwer. p. 1619.
AcelRx Pharmaceuticals, Inc., "AcelRx Pharmaceuticals Reports Positive Results from a Clinical Trial of Sublingual Sufentanil/Triazolam NanoTab™ Combination (ARX-03) in Treating Procedural Pain and Anxiety," 2 pages, Press Release (Jan. 12, 2009).
Actiq package insert (Cephalon) (2004).
Ahmad, S. et al., "Fentanyl HCl iontophoretic transdermal system versus intravenous morphine pump after gynecologic surgery," Arch. Gynecol. Obstet. 276:251-258 (2007).
Albert, J. M. et al., "Patient-Controlled Analgesia vs. Conventional Intramuscular Analgesia Following Colon Surgery," Diseases of the Colon & Rectum, 31(2):83-86 (1988).
Brown et al., "Procedural Sedation in the Acute Care Setting," Amer. Fam. Pharm. 71(1):85-90 (2005).
Chen et al., "Studies on Formulations of Fentanyl-Containing Oral Adhesive Tablets," Chin. J. Pharm. 28(3):129-131 (1997).
Christie, J. M. et al., "Dose-titration, multi-center study of oral transmucosal fentanyl citrate for the treatment of breakthrough pain in cancer patients using transdermal fentanyl for persistent pain," J Clin Oncol., 16(10):3238-3245 (1998).
Coda, B.A. et al., "Comparative efficacy of patient-controlled administration of morphine, hydromorphone, or sufentanil for the treatment of oral mucositis pain following bone marrow transplantation," Pain, 72:333-346 (1997).
Collins, L. M. C. et al., "The Surface Area of the Adult Human Mouth and Thickness of the Salivary Film Covering the Teeth and Oral Mucosa," J. Dent. Res. 66(8):1300-1302 (1987).
Coluzzi, P. H. et al., "Breakthrough Cancer Pain: A Randomized Trial Comparing Oral Transmucosal Fentanyl Citrate (OTFC) and Morphine Sulfate Immediate Release (MSIR)," Pain, 91(1-2):123-130 (2001).
Darwish, M. et al., "Absolute and Relative Bioavailability of Fentanyl Buccal Tablet and Oral Transmucosal Fentanyl Citrate," Journal of Clinical Pharmacology, 47:343-350 (2007).
Fisher, D.M. et al., "Pharmacokinetics of an Implanted Osmotic Pump Delivering Sufentanil for the Treatment of Chronic Pain," Anesthesiology, 99(4):929-937 (Oct. 2003).
Friedman et al., "Population study of triazolam pharmacokinetics," Br. J. Clin. Pharmacol., 22:639-642, 1986.
Goodwin et al., "Clinical Policy: Procedural Sedation and Analgesia in the Emergency Department," Annals Emerg. Med. 45(2) 177-196, 2005.
Grass, J., "Patient-Controlled Analgesia," Anesth. Analg., 101:S44-S61 (2005).
Halcion Package Insert, Apr. 2008.
Hicks et al., "The measurement of preoperative anxiety," J. Royal Soc. Med., 81: 517-519, 1988.
Hicks, R. et al., "USP Medication Safety Forum: Medication Errors Involving Patient-Controlled Analgesia," Joint Commission on Quality and Patient Safety, 34(12):734-742 (2008).
International Preliminary Report on Patentability for International Application No. PCT/US2007/000527, dated Feb. 24, 2009.
International Preliminary Report on Patentability for International Application No. PCT/US2007/000528, dated Jul. 8, 2008.
International Preliminary Report on Patentability for International Application No. PCT/US2007/000529, dated Jul. 8, 2008.
International Preliminary Report on Patentability for International Application No. PCT/US2007/089016, dated Jul. 7, 2009.
International Preliminary Report on Patentability for International Application No. PCT/US2007/089017, dated Jul. 7, 2009.
International Preliminary Report on Patentability for International Application No. PCT/US2007/089018, dated Jul. 7, 2009.
International Preliminary Report on Patentability for International Application No. PCT/US2010/052655, dated Apr. 17, 2012.
International Preliminary Report on Patentability for International Application No. PCT/US2009/064232, dated May 24, 2011.
International Preliminary Report on Patentability for International Application No. PCT/US2008/072445, dated Feb. 9, 2010.
International Search Report for International Application No. PCT/US2010/052655, mailed Apr. 4, 2011.
International Search Report for International Application No. PCT/US2007/089016, mailed Jun. 17, 2008.
International Search Report for International Application No. PCT/US2011/037401, mailed Aug. 19, 2011.
Jia et al., p. 10, in Novel controlled-release dosage forms for drugs, Chemical Industry Press (CIP), China (2005), Applicants' statement of relevance was considered.
Kraus et al., "Procedural sedation and analgesia in children," Lancet 367:766-780 (2006).
Kress et al. "Sedation and Analgesia in the Intensive Care Unit". Am J Respir Crit Care Med. 166; 2002:1024-1028.
Loeffler, "Oral Benzodiazepines and Conscious Sedation: A Review," J. Oral Maxillofacial. Surg., 50(9) 989-997, 1992.
Paix, A. et al., "Subcutaneous fentanyl and sufentanil infusion substitution for morphine intolerance in cancer pain management," Pain, 63:263-269 (1995).
Striebel, H. W. et al., "Patient-controlled intranasal analgesia (PCINA) for the management of postoperative pain: a pilot study," J Clin Anesth, 8:4-8 (1996).
Striebel, H. W. et al., "Patient-controlled intranasal analgesia: a method for noninvasive postoperative pain management," Anesth Analg, 83:548-551 (1996).
Supplementary European Search Report for European Application No. EP 08797363.2 dated Sep. 15, 2010.
Supplementary European Search Report for European Application No. EP 07716450.7 dated Apr. 6, 2011.
Van Vlymen et al., "Benzodiazepine Premedication," Anesthesiology 90:740-747, 1999.
Viscusi, E. R. et al., "An iontophoretic fentanyl patient-activated analgesic delivery system for postoperative pain: a double-blind, placebo-controlled trial," Anesth Analg., 102(1):188-194 (2006).
Viscusi, E. R. et al., "Patient-Controlled Transdermal Fentanyl Hydrochloride vs Intravenous Morphine Pump for Postoperative Pain: A randomized controlled trial," JAMA, 291(11):1333-1341 (2004).
Written Opinion for International Application No. PCT/US2007/000529, mailed Sep. 11, 2007.
Written Opinion for International Application No. PCT/US2007/000528, mailed Feb. 4, 2008.
Written Opinion for International Application No. PCT/US2007/000527, mailed Dec. 17, 2007.
Written Opinion for International Application No. PCT/US2007/089018, mailed Oct. 15, 2008.
Written Opinion for International Application No. PCT/US2007/089016, mailed Jun. 17, 2008.
Written Opinion for International Application No. PCT/US2007/089017, mailed Jun. 23, 2008.
Written Opinion for International Application No. PCT/US2008/072445, mailed Oct. 20, 2008.
Written Opinion for International Application No. PCT/US2009/064232, mailed Mar. 17, 2010.
Written Opinion for International Application No. PCT/US2010/027437, mailed Jun. 21, 2010.
Written Opinion for International Application No. PCT/US2010/052655, mailed Apr. 4, 2011.
Written Opinion for International Application No. PCT/US2011/037401, mailed Aug. 19, 2011.
Singapore Search Report issued in Singapore Patent Application No. 201103689.4 on May 3, 2013.

* cited by examiner

SUFENTANIL SOLID DOSAGE FORMS COMPRISING OXYGEN SCAVENGERS AND METHODS OF USING THE SAME

FIELD OF THE INVENTION

The present invention relates to compositions, methods and systems effective to minimize or eliminate the presence of oxidative degradation products in solid dosage forms comprising sufentanil. The solid dosage forms comprising sufentanil are packaged in a substantially oxygen impermeable container which includes at least one oxygen scavenging material.

BACKGROUND OF THE TECHNOLOGY

Many pharmaceutical formulations and reagents used in diagnostic evaluations are sensitive to oxygen and/or moisture. Exposure of such pharmaceutical formulations and reagents to oxygen may interfere with the stability and efficacy of the pharmaceutical agent or reagent.

The importance of providing pharmaceutical formulations in which an oxidation-susceptible active drug is protected against oxidative degradation, in particular, with prolonged storage or storage at elevated temperatures, is a concept well known to, and appreciated by, members of the pharmaceutical industry. Preservatives and antioxidants are often employed in the pharmaceutical formulation to address this problem.

Oxygen scavengers or displacement of oxygen with an inert gas in the headspace of a finished product has been used to reduce the generation of oxidative degradation products.

Degradation protectants for increasing the shelf-life of medical devices are described for example in U.S. Pat. No. 6,660,295 and United States Patent Publication Nos. 20010051180; 20040187438; and 20070084144. Oxygen scavenging packaging for pharmaceuticals and other oxygen sensitive products are described for example in United States Patent Publication Nos. 20020155233 and 20060076536.

Oxidative degradation of sufentanil has not been reported for liquid (Sufenta) or dry powder forms of sufentanil (Janssen Pharmaceuticals, and Johnson Matthey, Inc.). Surprisingly, oxidative degradation of sufentanil in low dose solid dosage forms prepared using aqueous and/or organic solvents has been observed.

There remains a need for development of specific pharmaceutical formulations and packaging systems to ensure that oxidation-susceptible drugs, such as sufentanil, can be formulated and stored in low dose solid dosage forms in a manner where oxidative degradation is minimized and the integrity of the active drug is maintained.

BRIEF SUMMARY OF THE INVENTION

Solid sufentanil drug dosage forms are provided in a primary package containing an oxygen scavenger, wherein the percentage of sufentanil oxidative degradation products is minimized or eliminated in solid sufentanil drug dosage forms packaged with an oxygen scavenger relative to solid sufentanil drug dosage forms packaged in the absence of an oxygen scavenger.

The packaged solid sufentanil drug dosage forms may be stored for at least 6 months under conditions selected from the group consisting of 5° C. and ambient humidity, 25° C. and 60% relative humidity and 40° C. and 75% relative humidity The packaged solid sufentanil drug dosage forms may have a mass of less than 30 mg or a volume of less than 30 mcL or a mass of less than 10 mg or a volume of less than 10 mcL and may comprise 5 mcg, 10 mcg, 15 mcg, 20 mcg, 30 mcg, 40 mcg, 50 mcg, 60 mcg, 70 mcg, 80 mcg or 100 mcg of sufentanil.

The packaged solid sufentanil drug dosage forms may be housed in a drug delivery dispenser such as a cartridge or a single dose applicator and the primary package may be a foil pouch.

Methods for preventing oxidative degradation of solid sufentanil drug dosage forms are also provided.

DETAILED DESCRIPTION OF THE INVENTION

I. Introduction

Provided herein are compositions, methods and systems effective to minimize or eliminate the presence of oxidative degradation products in solid dosage forms comprising sufentanil.

The following disclosure describes the compositions, methods and systems which constitute the invention. The invention is not limited to the specific dosage forms, devices, methodology, systems, kits or medical conditions described herein, as such may, of course, vary. It is also to be understood that the terminology used herein is for the purpose of describing particular embodiments only, and is not intended to limit the scope of the present invention.

It must be noted that as used herein and in the appended claims, the singular forms "a", "and", and "the" include plural references unless the context clearly dictates otherwise. Thus, for example, reference to "a drug formulation" includes a plurality of such formulations and reference to "a drug delivery device" includes systems comprising drug dosage forms and delivery devices for containment, storage and delivery of such dosage forms.

Unless defined otherwise, all technical and scientific terms used herein generally have the same meaning as commonly understood to one of ordinary skill in the art to which this invention belongs. Although any methods, devices and materials similar or equivalent to those described herein can be used in the practice or testing of the invention, the preferred methods, devices and materials are now described.

The publications discussed herein are provided solely for their disclosure prior to the filing date of the present application. Nothing herein is to be construed as an admission that the invention is not entitled to antedate such a disclosure by virtue of prior invention.

As used herein, the term "analgesic", is used with reference to any of a number of drugs used to relieve pain (achieve analgesia).

The term "analgesic drug" is used herein with reference to a drug which results in analgesia following administration to a subject, for example, sufentanil, or a sufentanil congener, such as alfentanil, fentanyl, lofentanil, carfentanil, remifentanil, trefentanil, or mirfentanil. The phrase "analgesic drug"

is not limited to sufentanil, a sufentanil congener, or formulations comprising sufentanil or a sufentanil congener.

The term "antioxidant" as used herein refers to a molecule or combination of molecules capable of slowing or preventing the oxidation of other molecules. Oxidation is a chemical reaction that transfers electrons from a substance to an oxidizing agent. Oxidation reactions can produce free radicals. Antioxidants typically terminate these chain reactions by removing free radical intermediates, and inhibit other oxidation reactions by being oxidized themselves.

The term "cartridge" is used herein with reference to a replaceable, single use disposable cartridge configured to hold one or more drug dosage forms, typically 40 and in some cases up to 200 drug dosage forms. The cartridge may comprise a smart cartridge recognition system with a physical keyed feature on the cartridge, a bar code on the cartridge, a magnetic tag on the cartridge, an RFID tag on the cartridge, an electronic microchip on the cartridge, or a combination thereof. The cartridge may comprise one or more shipping tablets, wherein at least one shipping tablet is dispensed prior to dispensing of a drug dosage form.

The term "replaceable cartridge" or "disposable cartridge" is used with reference to a cartridge for housing drug dosage forms and is typically configured to hold 40 or more drug dosage forms, wherein the cartridge is designed to be used in a dispensing device and discarded after use.

As used herein, the term "degradation" refers to any change in a "drug", "medication", or "pharmacologically active agent" (such as the sufentanil in a sufentanil-containing solid dosage form) during storage, for example by hydrolysis and/or oxidation of the drug or other components/excipients contained in the formulation.

As used herein, the term "degradation agent" refers to an agent which is exposed to a "drug", "medication", or "pharmacologically active agent" (such as the sufentanil in a sufentanil-containing solid dosage form) and causes an undesirable by-product, such as oxidizing agents or moisture (water).

As used herein, the term "degradation protectant" refers to any material which protects against degradation of a "drug", "medication", or "pharmacologically active agent" (such as the sufentanil in a sufentanil-containing solid dosage form), e.g., an oxygen scavenger, a desiccant, an anti-oxidant or a combination thereof.

The term "desiccant" is used herein with reference to a sorbant, in the form of a solid, liquid, or gel which has an affinity for water, and absorbs or adsorbs moisture from it's surrounding, thus controlling the moisture in the immediate environment.

The term "drug", "medication", "pharmacologically active agent", "therapeutic agent" and the like are used interchangeably herein and generally refer to any substance that alters the physiology of an animal and can be effectively administered by the oral transmucosal route.

The terms "formulation" and "drug formulation" as used herein refer to a physical composition containing at least one pharmaceutically active substance, which may be provided in any of a number of dosage forms for delivery to a subject. The dosage form may be provided to the patient as a lozenge, pill, capsule, membrane, strip, liquid, patch, film, gum, gel, spray or other form.

The term "hydrogel-forming preparation", means a solid formulation largely devoid of water which upon contact with an aqueous solution, e.g., a bodily fluid, and in particular that of the oral mucosa, absorbs water in such a way that it forms a hydrated gel in situ. The formation of the gel follows unique disintegration (or erosion) kinetics while allowing for release of the therapeutic agent over time. Additionally, the term "hydrogel-forming preparation" describes a solid formulation largely devoid of water which upon contact with bodily fluids, and in particular those in the oral cavity, transforms into a film that releases the drug. Such films increase the surface area available for drug release and absorption thus enabling faster absorption of the drug.

As used herein, the term "oxygen scavenger" refers to chemical substance that is added to a drug formulation or reagent in order to reduce or eliminate the generation of unwanted oxidation products. In general, an "oxygen scavenger" is effective to absorb oxygen. The term "oxygen scavenger" may be used interchangeably with the terms "oxygen scavenging element" and "oxygen absorber".

As used herein, the term "drug delivery dispenser" means the container which directly houses a drug, medication, or pharmacologically active agent. Examples include, a cartridge, a single dose applicator, a multiple dose applicator, a thermoplastic tray, a blister pack, a flexible container, and a rigid container.

As used herein, the term "drug dosage form" refers to a physical entity containing at least one drug, medication, or pharmacologically active agent for delivery to a subject. It may be in the form of a lozenge, pill, tablet, capsule, membrane, strip, powder, patch, film, gel, spray, gum or other form.

As used herein, the term "primary packaging" means the container which directly houses a drug, medication, or pharmacologically active agent. Examples include a foil pouch, a plastic container, a plastic film container, a blister pack, a glass container, and the like.

An exemplary foil pouch comprises one of more of aluminum, zinc, nickel, tin, iron, copper, chromium, cobalt, silver, gold, magnesium, manganese, lead, galvanized iron, and metal oxides.

The term "small volume sufentanil-containing drug dosage form" is used herein with reference to a small volume dosage form that contains an amount of sufentanil from about 2 micrograms (mcg) to about 200 mcg of sufentanil, e.g., 5 mcg, 10 mcg, 15 mcg, 20 mcg, 30 mcg, 40 mcg, 50 mcg, 60 mcg, 70 mcg, 80 mcg, 90 mcg, or 100 mcg or more of sufentanil.

The term "solid dosage form" or "solid drug dosage form" is used herein with reference to a dosage form that is a solid, e.g., a lozenge, a pill, a tablet, a membrane or a strip.

The term "subject" includes any subject, generally a mammal (e.g., human, canine, feline, equine, bovine, ungulate etc.), adult or child, in which treatment with a sufentanil-containing solid dosage form is desired. The terms "subject" and "patient" may be used interchangeably herein.

The term "substantially oxygen impermeable material" is used herein with reference to a material that allows the passage of little or no oxygen through the material.

Inhibition of Oxidative Degradation

Many drugs are susceptible to oxidative degradation. In particular, this is a problem when the drug is present as a low percentage of the overall drug formulation. In order to minimize or eliminate the presence of impurities in a drug formulation comprising an oxidation-susceptible active drug, and a dosage form made from such a formulation, e.g., a solid sufentanil dosage form, preservatives and antioxidants are often employed in the formulation to address this problem. In some cases, this is sufficient to minimize or eliminate the generation of oxidative degradation products. In other cases, additional measures may be required, such as use of a degradation protectant, e.g., an oxygen scavenger, when packaging the drug dosage form.

The oxygen-scavenger comprises a material suitable for effectively scavenging oxygen during drug storage, so that an oxidation-susceptible active drug, e.g., sufentanil, in a solid dosage form is not adversely affected by oxidation of the active drug.

Methods and compositions for protecting an oxidation-susceptible active drug, such as sufentanil, in a solid drug dosage form from oxidative degradation are disclosed. In some cases, the methods involve inclusion of an oxygen scavenger in the packaging for the drug dosage form. In this manner, drug dosage forms, e.g., sufentanil tablets, are produced and stored under conditions wherein the active drug is protected from oxidative degradation, thus facilitating storage of the drug dosage form over extended periods of time.

Additional protection against oxygen exposure may be afforded by employment of packaging techniques designed to minimize exposure of the active drug to oxygen and/or moisture. Exemplary packaging techniques include use of primary packaging wherein more than one oxygen scavenging material is employed alone or in combination with use of a desiccant.

In one exemplary approach, an anti-oxidant such as BHT is included in the drug formulation, a drug delivery dispenser (e.g., a cartridge) houses the drug dosage form(s), and an oxygen scavenger is included in the primary packaging for the drug delivery dispenser, wherein gas exchange is possible between the drug delivery dispenser and the oxygen scavenger in the primary package.

In another exemplary approach, an anti-oxidant such as BHT is included in the drug formulation, a desiccant is included in the drug delivery dispenser (e.g., a cartridge) which houses the drug dosage form(s), and an oxygen scavenger is included in the primary packaging wherein gas exchange is possible between the drug delivery dispenser and primary package.

In a related approach, the oxidative degradation of a drug such as sufentanil is reduced or eliminated by providing the drug in an oxygen impermeable primary package, such as a foil pouch, which comprises at least one oxygen scavenging material.

In yet another embodiment, the antioxidant and/or the desiccant material are incorporated into the material that is used to make the drug delivery dispenser or primary packaging. In another embodiment, drug delivery dispenser or primary packaging material is comprised of an antioxidant packaging material.

In a preferred embodiment, the drug delivery dispenser is comprised of a material that does not generate degradation products upon exposure to a solid dosage form containing a pharmaceutically active agent, such as sufentanil. Exemplary materials for use in packaging include, glass, polypropylene, polyethylene (e.g., high density polyethylene (HDPE) or low density polyethylene (LDPE), polyester, polystyrene, polyamide, fluoro polymers such as ACLAR®, ethylene covinyl alcohol (EVOH), polycarbonate, polyurethane, polyvinylidene chloride (PVDC), polyvinyl alcohol (PVA) copolymers thereof, or blends thereof.

Exemplary materials for use in manufacture of single dose applicators, include but are not limited to TecoFlex EG 80A, Polyisoprene, Zylar 220; NAS 30 (NEOS NOVA), Versaflex, CL2242 (GLS Corp), KR01 (Chevron Phillips), Housing Polymer, Delrin® acetal (DuPont), Polyester (Valox; Celanex), Polypropylene, Pro Fax PD702 (Basell) and the like.

Antioxidants

Antioxidants commonly employed in pharmaceutical formulations include, but are not limited to, vitamin E, ascorbic acid, BHT (butylated hydroxytoluene), BHA (butylated hydroxyanisole), propyl gallate, ascorbyl palmitate, biflavonoids and the like. An antioxidant may be included in the formulation of an oxidation-susceptible drug, such as sufentanil, in particular, when provided in low dose solid dosage forms.

Oxygen Scavengers

Suitable oxygen scavengers include any organic or inorganic material that can absorb oxygen, for example, iron oxide powders, ferrous salts such as ferrous sulfate or ferrous chloride, sulfites, bisulfites, reducing sulfur compounds such as dithionite, ascorbic acid and/or their salts, erythorbic acid and/or their salts, reducing organic compounds such as catechol and hydroquinone, butylated hydroxytoluene (BHT), butylated hydroxyanisole (BHA). See, e.g. U.S. Patent Publication Nos. 20060076536, 20070084144, 20060260967.

A number of oxygen scavengers and moisture absorbents are commercially available and may be purchased alone or in packages, e.g., StabilOx® (Multisorb Technologies), cyclohexene methyl acrylated (EMCM) polymer (Chevron-Phillips Chemical Company) or Ciba's Specialty Chemical's SHELFPLUS™).

An oxygen scavenger may be included in the packaging in the form of pellets, canisters, packets, capsules, powders, solid materials, tablets, or as part of the packaging material itself.

Desiccants

Any commercial desiccant may be used, e.g., in the packaging of a solid sufentanil dosage form. Desiccants may be provided as pellets, canisters, packets, capsules, powders, solid materials, papers, boards, tablets, adhesive patches and films, and can be formed for specific applications, including injection moldable plastics. Exemplary solid desiccants include, silica gel (sodium silicate), alumino-silicate, activated alumina, zeolite, molecular sieves, montmorillonite clay, calcium oxide and calcium sulfate.

In some embodiments, one or more desiccants may be employed in a drug delivery dispenser, e.g., within a cartridge or single dose applicator containing drug dosage forms, or inside the primary packaging for the drug-containing drug delivery dispenser, as a means for protecting solid drug dosage forms from moisture. Exemplary locations include, in or adjacent the dosage form or delivery pathway, in or adjacent a tablet magazine or cartridge, in or adjacent other components of a dispensing device, formed as an injection molded component of a dispensing device, and any other location within or without the device wherein the desiccant is in sufficiently close proximity to the drug dosage form to pick up moisture.

Solid Dosage Forms

In general, small volume solid dosage forms containing from about 2 mcg to about 200 mcg of sufentanil are used for oral transmucosal drug delivery. The dosage forms contain sufentanil, alone or in combination with another drug, e.g., a benzodiazepine such as triazolam.

The process for manufacture of solid dosage forms, e.g., tablets, pills, capsules, strips, films, powders, lozenges, membranes, patches, film or other forms, comprising sufentanil, typically involves the use of an aqueous and/or organic solvent.

The sufentanil-containing solid dosage forms have a mass of less than 100 mg or a volume of less than 100 mcL. More specifically, the dosage forms have a mass of less than 100 mg, 90 mg, 80 mg, 70 mg, 60 mg, 50 mg, 40 mg, 30 mg, 29 mg, 28 mg, 27 mg, 26 mg, 25 mg, 24 mg, 23 mg, 22 mg, 21 mg, 20 mg, 19 mg, 18 mg, 17 mg, 16 mg, 15 mg, 14 mg, 13 mg, 12 mg, 11 mg, 10 mg, 9 mg, 8 mg, 7 mg, 6 mg or 5 mg or a volume of less than 100 mcL, 90 mcL, 80 mcL, 70 mcL, 60 mcL, 50 mcL, 40 mcL, 30 mcL, 29 mcL, 28 mcL, 27 mcL, 26 mcL, 25 mcL, 24 mcL, 23 mcL, 22 mcL, 21 mcL, 20 mcL, 19 mcL, 18 mcL, 17 mcL, 16 mcL, 15 mcL, 14 mcL, 13 mcL, 12 mcL, 11 mcL, 10 mcL, 9 mcL, 8 mcL, 7 mcL, 6 mcL or 5 mcL. In one exemplary embodiment, the tablets have a mass of 5.85 mg. The dosage forms may have bioadhesive characteristics and may form a hydrogel upon contact with an aqueous solution.

Typical formulations for preparation of sufentanil-containing solid dosage forms and methods of making them are described in U.S. application Ser. Nos. 11/825,251 and 11/650,227, expressly incorporated by reference herein. An exemplary formulation is bioadhesive and comprises from about 0.04% to about 4% sufentanil, from about 0.08% to about 1.7% sufentanil or from abut 0.1% to about 2.0% sufentanil, e.g., about 0.04%, 0.08%, 0.1%, 0.2%, 2.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.1%, 1.2%, 1.3%, 1.4%, 1.5%, 1.6%, 1.7%, 1.8%, 1.9%, 2.0%, 2.2%, 2.2%, 2.4%, 2.5%, 2.6%, 2.8%, 3.0%, 3.2%, 3.5% or 4% sufentanil. In general, the formulation comprises: a non-ordered mixture of a pharmaceutically active amount of a drug; and a bioadhesive material which provides for adherence to the oral mucosa of the subject. Dissolution of a dosage form comprising the formulation is generally independent of pH, e.g., over a pH range of about 4 to 8.

Numerous suitable nontoxic pharmaceutically acceptable carriers for use in sufentanil-containing solid dosage forms can be found in Remington's Pharmaceutical Sciences, 17th Edition, 1985.

It will be understood that a sufentanil-containing formulation is converted into sufentanil-containing solid dosage forms for delivery to a subject using procedures routinely employed by those of skill in the art, such as direct compression, wet granulation, etc. The process for preparation of sufentanil-containing solid dosage forms typically involves use of aqueous and/or organic solvents and is optimized for each formulation in order to achieve high dose content uniformity.

Cartridges and Single Dose Applicators

The cartridge for housing drug dosage forms may be cylindrical, disk-shaped, helical, rectilinear, non-ordered, or may take the form of any assemblage of drug dosage forms that allows a drug dispensing device to dispense them in a controlled manner.

In one embodiment of the invention, a cartridge may hold sufficient drug dosage forms for 1-5 days of treatment, e.g., 40 tablets useful for 48 to 72 hours of treatment.

To prevent unused drug dosage forms from absorbing moisture or otherwise becoming exposed to moisture prior to use, a cartridge or other drug dispensing device may provide a means of sealing the drug dosage forms from exposure to moisture. This may accomplished by use of a cartridge that contains a desiccant or other absorbent or adsorbent material to absorb or adsorb moisture that penetrates the cartridge either prior to use or during normal use.

The desiccant is a sorbant, in the form of a solid, liquid, or gel that has an affinity for water, and absorbs or adsorbs moisture from the surrounding, thus controlling the moisture in the immediate environment. Any commercial desiccant may be used. Such commercial desiccants typically take the form of pellets, canisters, packets, capsules, powders, solid materials, papers, boards, tablets, adhesive patches, and films, and can be formed for specific applications, including injection moldable plastics. There are many types of solid desiccants, including silica gel (sodium silicate, which is a solid, not a gel), alumino-silicate, activated alumina, zeolite, molecular sieves, montmorillonite clay, calcium oxide and calcium sulfate, or others, any of which may be used in practicing the present invention.

In one embodiment, a single dose applicator (SDA) is used as the drug delivery dispenser for a solid sufentanil drug dosage form. In this embodiment, the SDA is contained in a primary package which is not oxygen permeable. In another embodiment, the SDA is contained in a primary package which is oxygen permeable. In yet another embodiment, the primary package is contained in a secondary package which is not oxygen permeable.

The SDA may contain the dosage form within, may have the drug dosage form attached or affixed to it, and/or may afford a seal against moisture, humidity, and light. The single dose applicator may be manually manipulated by a patient, healthcare provider, or other user to place the dosage form in the proper location for drug delivery.

The SDA may be provided as a pair of forceps, a syringe, a stick or rod, a straw, a pad, a capsule, a cup, a spoon, a strip, a tube, an applicator, a dropper, a patch, an adhesive pad, an adhesive film, a sprayer, an atomizer, or any other form suitable for the application of a single drug dosage form to the oral mucosa of a subject, e.g., the oral mucosa in the sublingual space. As will be understood by those of skill in the art, the SDA design may vary, so long as it is effective to place a drug dosage form, such as a tablet, in the desired location, e.g., in the sublingual space, in a manner that preserves integrity of the drug dosage form in the dispensing process. After use, the SDA is disposed of.

The dosage form may be provided in a drug delivery dispenser that consists of molded plastic or laminate that has indentations ("blisters") into which a dosage form is placed, referred to herein as a "blister pack". A blister pack may or may not have pre-formed or molded parts and may be used to package an SDA of any type.

SDAs may be provided in a child resistant multiple drug dispenser (MDD), which may serve to dispense the dosage forms housed therein or may be used for storage of a plurality of SDAs.

In one embodiment, an SDA serves as the drug delivery dispenser and an MDD serves as the primary package.

The dosage forms inside the SDA and MDD remain dry prior to dispensing a drug dosage form.

A desiccant may or may not be included in the drug delivery dispenser and an oxygen scavenger is typically included in the primary package.

Utility.

The presence of impurities in a pharmaceutical formulation that remain with the active pharmaceutical ingredient (API), develop during formulation, or develop upon aging of either API or formulated drug dosage forms can be problematic. The presence of such impurities even in small amounts may influence the efficacy and safety of a pharmaceutical product. Impurities in pharmaceutical products must be analyzed and identified. It is preferable that the total amount of active drug (e.g., sufentanil) degradation products not exceed 5%, 4%, 3%, 2%, 1%, 0.9%, 0.8%, 0.7%, 0.6%, 0.5%, 0.4%, 0.3%, 0.2%, 0.1% or less of the amount of the active drug substance in a given drug dosage form. The International Conference on Harmonization (ICH) provides guidelines regarding the control of impurities.

The reduction or elimination of oxidative degradation products in drug dosage forms, e.g., solid dosage forms comprising sufentanil, can be achieved by inclusion of oxygen scavengers in the packaging for the drug dosage forms.

The preceding merely illustrates the principles of the invention. It will be appreciated that those skilled in the art will be able to devise various arrangements which, although not explicitly described or shown herein, embody the principles of the invention and are included within its spirit and scope. Furthermore, all statements herein reciting principles, aspects, and embodiments of the invention as well as specific examples thereof, are intended to encompass both structural and functional equivalents thereof, both currently known equivalents and equivalents developed in the future. The scope of the present invention, therefore, is not intended to be limited to the exemplary embodiments shown and described herein.

EXAMPLES

Example 1

Stability Studies with Solid Sufentanil Dosage Forms in the Presence and Absence of Oxygen Scavengers A study was carried out to evaluate the stability of tablets comprising 5 mcg of sufentanil, having a mass of 5.85 mg following storage in high density polyethylene (HDPE) bottles for 0.5 months, 1 month, 2 months and 3 months under different environmental conditions with or without oxygen scavengers.

The storage conditions were the following:
(1) 5° C. at ambient humidity
(2) 25° C. and 60% relative humidity (RH)
(3) 40° C. and 75% relative humidity (RH)

The 5 mcg sufentanil formulation included 0.128% sufentanil citrate in a matrix of mannitol, hydroxypropylmethyl cellulose, stearic acid, magnesium stearate, dicalcium phosphate and butylated hydroxyl toluene (BHT), as follows.

| Component | Amount Per Tablet (mg) | % in the Formulation |
|---|---|---|
| Sufentanil Citrate | 0.0075 | 0.128 |
| Mannitol SD100 | 4.131 | 70.62 |
| Di-Calcium Phosphate di-hydrate | 1.170 | 20.00 |
| HPMC K4M Premium CR | 0.176 | 3.00 |
| Stearic Acid | 0.293 | 5.00 |
| Mg Stearate | 0.059 | 1.00 |
| BHT | 0.015 | 0.25 |
| Total | 5.850 | 100.00 |

The HPLC profile of solid sufentanil dosage forms stored with or without oxygen scavengers (StabilOx®; Multisorb) was evaluated following storage in HDPE bottles at T=0 and at 2 weeks, 1 month, 2 months, 3 months and 6 months. The stability of sufentanil was evaluated by HPLC analysis under the conditions set forth below. As will be understood by those of skill in the art, the conditions set forth below are exemplary conditions for HPLC analysis and are not intended to be limiting as to other possible methods of analysis.

| Chromatographic System and Conditions | |
|---|---|
| Column | Waters XTerra RP18, 5 μm, 250 mm × 4.6 mm |
| Detection | 235 nm |
| Column Temperature | 30° C. |
| Injection Volume | 100 μL |
| Flow Rate | 1.0 mL/min |
| Mobile Phase | MP A: 20 mM Ammonium Phosphate Buffer (pH 7.2) MP B: Acetonitrile |
| Run Time | 55 min |

| Gradient Conditions | | |
|---|---|---|
| Time (min) | Mobile Phase A | Mobile Phase B |
| 0 | 75 | 25 |
| 5 | 75 | 25 |
| 35 | 30 | 70 |
| 49 | 30 | 70 |
| 50 | 75 | 25 |
| 55 | 75 | 25 |

Samples analyzed for sufentanil degradation products were a composite of NanoTabs™ that provided about 50 ug/mL (of sufentanil) in solution. In carrying out the method, the number of NanoTabs™ and the volume needed to achieve a nominal concentration of about 50 μg/mL was calculated, then an amount of extraction solution equivalent to approximately 30% of the sample volume was pipetted into the container, the mixture was sonicated for 15 minutes, followed by dilution to volume with 20 mM ammonium phosphate buffer and thorough mixing. A glass syringe was used to filter the supernatant solution through a 0.45 μm Millipore Millex Nylon syringe filter. The first mL of filtrate was discarded, then the remainder was used to fill HPLC 9 mm TFE/SIL/TFE blue cap containers, followed by HPLC analysis.

Table 1A shows the results of HPLC analysis of solid sufentanil dosage forms for the presence of degradation products following storage at 5° C. and ambient humidity, as evidenced by peaks at relative retention times (RRT) of 0.37, 0.50 and 0.56 following storage in HDPE bottles for 2 weeks, 1 month, 2 months, 3 months and 6 months.

TABLE 1A

Stability Evaluation of 5 mcg Sufentanil Tablets at 5° C. and ambient humidity.

| ~RRT | T = 0 | 2 wks 5° C. | 1 mo 5° C. | 2 mo 5° C. | 3 mo 5° C. | 6 mo 5° C. |
|---|---|---|---|---|---|---|
| 0.37 | | | | | | |
| 0.50 | 0.39% | 0.53% | 0.59% | 0.68% | 0.84% | 1.10% |
| 0.56 | 0.19% | 0.24% | 0.25% | 0.32% | 0.39% | 0.50% |
| % Total Deg | 0.58% | 0.77% | 0.84% | 1.00% | 1.23% | 1.60% |

Total Deg. = Total degradation is reported as a percentage (%) of total sufentanil peak area.

Table 1B shows the results of HPLC analysis of solid sufentanil dosage forms for the presence of degradation products following storage at 5° C. and ambient humidity, as evidenced by peaks at relative retention times (RRT) of 0.37, 0.50 and 0.56 following storage in HDPE bottles containing an oxygen scavenger (Stabilox®; Multisorb Technologies) at T=0, 2 weeks, 1 month, 2 months, 3 months and 6 months.

TABLE 1B

Stability Evaluation of 5 mcg Sufentanil Tablets Stored at 5° C./ambient humidity in HDPE Bottles Containing Oxygen Scavengers.

| ~RRT | T = 0 | 2 wks 5° C. | 1 mo 5° C. | 2 mo 5° C. | 3 mo 5° C. | 6 mo 5° C. |
|---|---|---|---|---|---|---|
| 0.37 | | <0.1 | <0.1 | | | |
| 0.50 | 0.16% | <0.1 | 0.22% | 0.21% | 0.18% | 0.14% |
| 0.56 | | <0.1 | 0.13% | 0.11% | 0.10% | |
| % Total Deg | 0.16% | 0.00% | 0.35% | 0.32% | 0.28% | 0.14% |

Figure 1:
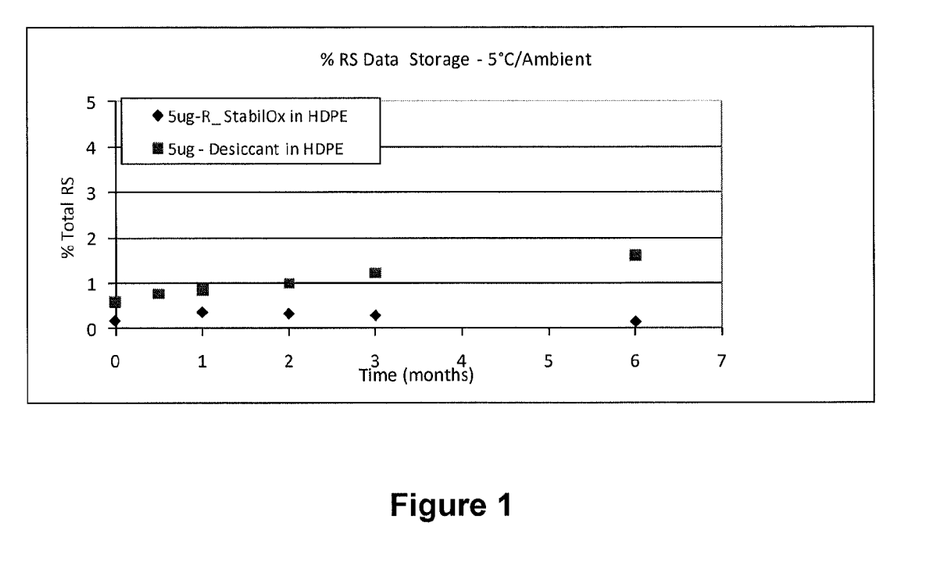
FIG. 1 provides a graphic depiction of % Total RS versus time (0, 0.5, 1, 2, 3 and 6 months) for 5 mcg sufentanil dosage forms made using a standard formulation following storage at 5° C. and ambient humidity in HDPE bottles containing desiccant (5 ug—Desiccant in HDPE) or in HDPE bottles containing an oxygen scavenger (5 ug-R_Stabilox in HDPE).

FIG. 1 shows the % Total RS versus time (0, 0.5, 1, 2 and 3 months), for 5 mcg sufentanil dosage forms made using a standard formulation following storage at 5° C. and ambient humidity in HDPE bottles alone (5 ug) or containing an oxygen scavenger (Stabilox®; Multisorb Technologies; 5 ug-R). The designation "% Total RS" (% total related substances) means the same thing and is used interchangeably herein with the term "% SDP (percent sufentanil degradation products) which is the percentage of the peak area for "related substances" (sufentanil degradation products) relative to the total peak area for sufentanil.

Table 2A shows the results of HPLC analysis of solid sufentanil dosage forms for the presence of degradation products following storage at 25° C. and 60% RH, as evidenced by peaks at relative retention times (RRT) of 0.37, 0.50, 0.54 and 0.56 following storage in HDPE bottles containing an oxygen scavenger (Stabilox®), at T=0, 2 weeks, 1 month, 2 months, 3 months and 6 months.

TABLE 2A

Stability Evaluation of 5 mcg Sufentanil Tablets at 25° C. and 60% RH in HDPE Bottles Containing Stabilox ®.

| ~RRT | T = 0 | 2 wks 25° C./60% RH | 1 mo 25° C./60% RH | 2 mo 25° C./60% RH | 3 mo 25° C./60% RH | 6 mo 25° C./60% RH |
|---|---|---|---|---|---|---|
| 0.37 |  |  |  | 0.11% | 0.11% | 0.19% |
| 0.50 | 0.39% | 0.86% | 0.95% | 1.28% | 1.46% | 1.69% |
| 0.54 |  |  |  |  |  | <0.1% |
| 0.56 | 0.19% | 0.40% | 0.44% | 0.61% | 0.68% | 0.76% |
| % Total Deg | 0.58% | 1.26% | 1.39% | 2.00% | 2.25% | 2.64% |

Table 2B shows the results of HPLC analysis of solid sufentanil dosage forms for the presence of degradation products following storage at 25° C. and 60% RH, as evidenced by peaks at relative retention times (RRT) of 0.37, 0.50 and 0.56 following storage in HDPE bottles containing an oxygen scavenger (Stabilox®), at T=0, 2 weeks, 1 month, 2 months, 3 months and 6 months.

TABLE 2B

Stability Evaluation of 5 mcg Sufentanil Tablets Stored at 25° C. and 60% RH in HDPE Bottles Containing Oxygen Scavengers.

| ~RRT | T = 0 | 2 wks 25° C./60% RH | 1 mo 25° C./60% RH | 2 mo 25° C./60% RH | 3 mo 25° C./60% RH | 6 mo 25° C./60% RH |
|---|---|---|---|---|---|---|
| 0.37 |  | <0.1 | <0.1 | <0.1 |  |  |
| 0.50 | 0.16% | <0.1 | <0.1 | <0.1 | 0.10% | 0.13% |
| 0.56 |  | <0.1 | <0.1 | <0.1 |  |  |
| % Total Deg | 0.16% | 0.00% | 0.00% | 0.00% | 0.10% | 0.13% |

Figure 2:
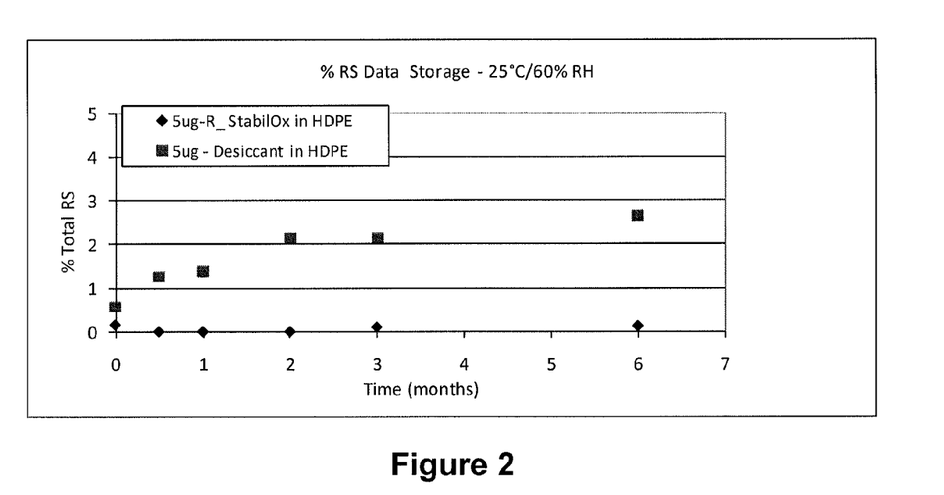
FIG. 2 provides a graphic depiction of % Total RS versus time (0, 0.5, 1, 2, 3 and 6 months) for 5 mcg sufentanil dosage forms made using a standard formulation following storage at 25° C. and 60% relative humidity in HDPE bottles containing desiccant (5 ug—Desiccant in HDPE) or in HDPE bottles containing an oxygen scavenger (5 ug-R_Stabilox in HDPE).

FIG. 2 shows the % Total RS versus time (0, 0.5, 1, 2 and 3 months) for 5 mcg sufentanil dosage forms made using a standard formulation following storage at 25° C. and 60% humidity in HDPE bottles alone (5 ug) or containing an oxygen scavenger (5 ug-R).

Table 3A shows the results of analysis of solid sufentanil dosage forms for the presence of degradation products following storage at 40° C. and 75% RH, as evidenced by peaks at relative retention times (RRT) of 0.37, 0.50, 0.54 and 0.56 following storage in HDPE bottles at T=0, 2 weeks, 1 month, 2 months, 3 months and 6 months.

TABLE 3A

Stability Evaluation of 5 mcg Sufentanil Tablets Stored at 40° C. and 75% RH in HDPE Bottles.

| ~RRT | T = 0 | 2 wks 40° C./75% RH | 1 mo 40° C./75% RH | 2 mo 40° C./75% RH | 3 mo 40° C./75% RH | 6 mo 40° C./75% RH |
|---|---|---|---|---|---|---|
| 0.37 |  | 0.11% | 0.22% | 0.38% | 0.43% | 0.42% |
| 0.50 | 0.39% | 0.86% | 0.92% | 1.09% | 1.12% | 1.00% |
| 0.54 |  |  |  |  |  | 0.29% |
| 0.56 | 0.19% | 0.46% | 0.52% | 0.67% | 0.64% | 0.46% |
| % Total Deg | 0.58% | 1.43% | 1.66% | 2.14% | 2.19% | 2.17% |

Table 3B shows the results of HPLC analysis of solid sufentanil dosage forms for the presence of degradation products following storage at 40° C. and 75% RH, as evidenced by peaks at relative retention times (RRT) of 0.37, 0.50 and 0.56 following storage in HDPE bottles containing an oxygen scavenger (Stabilox®), at T=0, 2 weeks, 1 month, 2 months, 3 months and 6 months.

TABLE 3B

Stability Evaluation of 5 mcg Sufentanil Tablets Stored at 40° C. and 75% RH in HDPE Bottles Containing Oxygen Scavengers.

| ~RRT | T = 0 | 2 wks 40° C./75% RH | 1 mo 40° C./75% RH | 2 mo 40° C./75% RH | 3 mo 40° C./75% RH | 6 mo 40° C./75% RH |
|---|---|---|---|---|---|---|
| 0.37 |  | <0.1 | <0.1 | <0.1 |  |  |
| 0.50 | 0.16% | <0.1 | <0.1 | <0.1 |  | 0.56% |
| 0.56 |  | 0.14% | 0.28% | 0.39% | 0.32% |  |
| % Total Deg | 0.16% | 0.14% | 0.28% | 0.39% | 0.32% | 0.56% |

Figure 3:
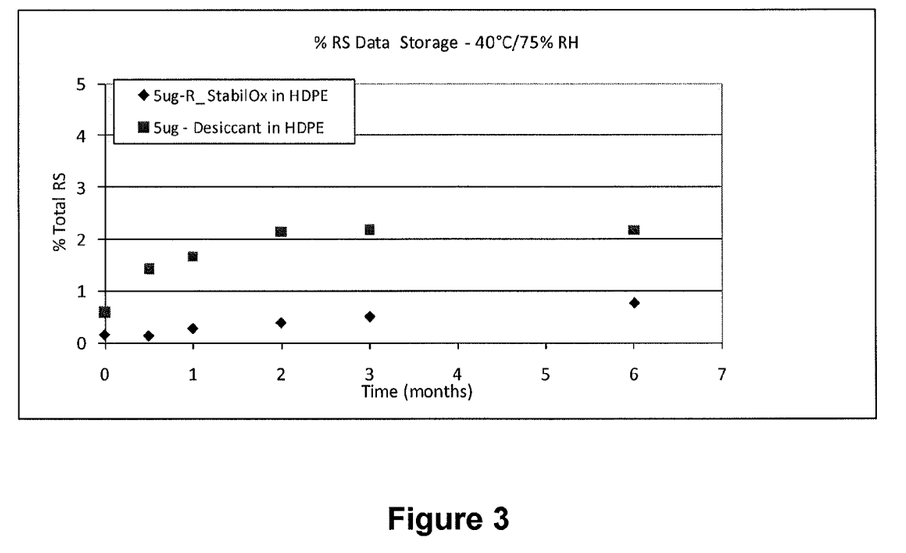
FIG. 3 provides a graphic depiction of % Total RS versus time (0, 0.5, 1, 2, 3 and 6 months) for 5 mcg sufentanil dosage forms made using a standard formulation following storage at 40° C. and 75% relative humidity in HDPE bottles containing desiccant (5 ug—desiccant in HDPE) or in HDPE bottles containing an oxygen scavenger (5 ug-R_Stabilox in HDPE).

FIG. 3 shows the % Total RS versus time (0, 0.5, 1, 2 and 3 months) for 5 mcg sufentanil dosage forms made using a standard formulation following storage at 40° C. and 75% humidity in HDPE bottles alone (5 ug) or containing an oxygen scavenger (5 ug-R).

Table 4 shows the results of HPLC analysis of solid sufentanil dosage forms for the presence of degradation products, following storage at 5° C. and ambient humidity in HDPE bottles+Stabilox® or without Stabilox®, reported as % Total RS versus time.

TABLE 4

Stability Evaluation of 5 mcg Sufentanil Tablets Stored at 5° C. and Ambient Humidity in HDPE Bottles With or Without Oxygen Scavengers.

| Time (months) | % Total RS (+ Stabilox ®) | % Total RS (without Stabilox ®) |
|---|---|---|
| 0 | 0.16 | 0.58 |
| 0.5 |  | 0.77 |
| 1 | 0.35 | 0.84 |
| 2 | 0.32 | 1.00 |
| 3 | 0.28 | 1.23 |
| 6 | 0.14 | 1.6 |

Table 5 shows the results of HPLC analysis of solid sufentanil dosage forms for the presence of degradation products following storage at 25° C. and 60% RH in HDPE bottles for 0, 0.5, 1, 2, 3 and 6 months in HDPE bottles+Stabilox® or without Stabilox®, reported as % Total RS versus time.

TABLE 5

Stability Evaluation of 5 mcg Sufentanil Tablets Stored at 25° C. and 60% RH in HDPE Bottles with or without Oxygen Scavengers.

| time (months) | % Total RS (+ Stabilox ®) | % Total RS (without Stabilox ®) |
|---|---|---|
| 0 | 0.16 | 0.58 |
| 0.5 | 0 | 1.26 |
| 1 | 0 | 1.39 |
| 2 | 0 | 2.15 |
| 3 | 0.1 | 2.15 |
| 6 | 0.13 | 2.64 |

Table 6 shows the results of HPLC analysis of solid sufentanil dosage forms for the presence of degradation products following storage at 40° C. and 70% RH, in HDPE bottles+Stabilox® or without Stabilox®, reported as % Total RS versus time.

TABLE 6

Stability Evaluation of 5 mcg Sufentanil Tablets Stored at 40° C. and 75% RH in HDPE Bottles with or without Oxygen Scavengers.

| time (months) | % Total RS (+ Stabilox ®) | % Total RS (without Stabilox ®) |
|---|---|---|
| 0 | 0.16 | 0.58 |
| 0.5 | 0.14 | 1.43 |
| 1 | 0.28 | 1.66 |
| 2 | 0.39 | 2.14 |
| 3 | 0.51 | 2.19 |
| 6 | 0.77 | 2.17 |

The results presented in Example 1 show that the generation of sufentanil degradation products following storage of solid sufentanil dosage forms is reduced or eliminated by storing the solid sufentanil drug dosage forms (e.g., tablets) in the presence of an oxygen scavenger.

Example 2

Stability Studies with Solid Sufentanil Dosage Forms in the Presence of Desiccant or Oxygen Scavengers A study was carried out to evaluate the stability of tablets comprising 5 mcg of sufentanil, having a mass of 5.85 mg following storage in high density polyethylene (HDPE) bottles for 0.5 months, 1 month, 2 months, 3 months and 6 months under different environmental conditions in the presence of oxygen scavengers or desiccant.

The desiccant used was 1 g silica gel Sachet®.

The storage conditions were the following:

5° C. at ambient humidity;

25° C. and 60% relative humidity (RH); and

40° C. and 75% relative humidity (RH).

The sufentanil formulation and details of the HPLC procedure are provided in Example 1, above.

The HPLC profile of solid sufentanil dosage forms stored with StabilOx® or desiccant was evaluated following storage in HDPE bottles for 0.5 months, 1 month, 2 months, 3 months and 6 months.

Table 7 shows the results of HPLC analysis of solid sufentanil dosage forms for the presence of degradation products following storage in HDPE bottles at 5° C. and ambient humidity, reported as % total SDP at T=0 and at 0.5 months, 1 month, 2 months, 3 months and 6 months in the presence of an oxygen scavenger (5 ug-R_Stabilox®), or desiccant (5 ug—Desiccant).

TABLE 7

Stability Evaluation of 5 mcg Sufentanil Tablets Stored at 5° C. in HDPE Bottles With Oxygen Scavengers or Desiccant.

| Time (months) | 5ug-R_Stabilox ® in HDPE | 5ug - Desiccant in HDPE |
|---|---|---|
| 0 | 0.16 | 0.58 |
| 0.5 | | 0.77 |
| 1 | 0.35 | 0.84 |
| 2 | 0.32 | 1.00 |
| 3 | 0.28 | 1.23 |
| 6 | 0.14 | 1.6 |

Table 8 shows the results of HPLC analysis of solid sufentanil dosage forms for the presence of degradation products following storage in HDPE bottles at 25° C. and 60% RH, reported as % total SDP at T=0 and at 0.5 months, 1 month, 2 months, 3 months and 6 months in the presence of an oxygen scavenger (5 ug-R_Stabilox®), or desiccant (5 ug—Desiccant).

TABLE 8

Stability Evaluation of 5 mcg Sufentanil Tablets Stored at Stored at 25° C. and 60% RH in HDPE Bottles With Oxygen Scavengers or Desiccant.

| Time (months) | 5ug-R_Stabilox ® in HDPE | 5ug - Desiccant in HDPE |
|---|---|---|
| 0 | 0.16 | 0.58 |
| 0.5 | 0 | 1.26 |
| 1 | 0 | 1.39 |
| 2 | 0 | 2.15 |
| 3 | 0.1 | 2.15 |
| 6 | 0.13 | 2.64 |

Table 9 shows the results of HPLC analysis of solid sufentanil dosage forms for the presence of degradation products following storage in HDPE bottles at 40° C. and 75% RH, reported as % total SDP at T=0 and at 0.5 months, 1 month, 2 months, 3 months and 6 months in the presence of an oxygen scavenger (5 ug-R_Stabilox®), or desiccant (5 ug—Desiccant).

TABLE 9

Stability Evaluation of 5 mcg Sufentanil Tablets Stored at Stored at 40° C. and 75% RH in HDPE Bottles With Oxygen Scavengers or Desiccant.

| Time (months) | 5ug-R_Stabilox ® in HDPE | 5ug - Desiccant in HDPE |
|---|---|---|
| 0 | 0.16 | 0.58 |
| 0.5 | 0.14 | 1.43 |
| 1 | 0.28 | 1.66 |
| 2 | 0.39 | 2.14 |
| 3 | 0.51 | 2.19 |
| 6 | 0.77 | 2.17 |

Example 3

Stability Studies with Solid Sufentanil Dosage Forms in Cartridges in the Presence of Oxygen Scavengers Further studies were carried out on stability of solid sufentanil dosage forms following storage in cartridges comprising 40 tablets and StabilOx®. A study was carried out to evaluate the stability of tablets comprising 10 mcg of sufentanil, having a mass of 5.85 mg, following storage in cartridges for 1 month, 2 months, and 3 months under different storage conditions in the presence of an oxygen scavenger (Stabilox®).

The storage conditions were the following:
25° C. and 60% relative humidity (RH); and
40° C. and 75% relative humidity (RH).

The sufentanil formulation was the following: 0.256% sufentanil citrate in matrix of mannitol, hydroxypropylmethyl cellulose, stearic acid, magnesium stearate, dicalcium phosphate and butylated hydroxyl toluene (BHT).

The HPLC profile of solid sufentanil dosage forms stored with oxygen scavengers (an (Stabilox®) was evaluated following storage in cartridges for T=0, 1 month, 2 months and 3 months, using the conditions provided in Example 1, above.

Tables 10A and B show the results of HPLC analysis of solid sufentanil dosage forms for the presence of degradation products following storage in HDPE bottles or cartridges made of various materials and containing an oxygen scavenger, at 25° C. and 60% RH, as evidenced by peaks at relative retention times (RRT) of 0.36, 0.49/0.50 and 0.54/0.55 at T=0, 1 month, 2 months and 3 months.

TABLE 10A

Stability Evaluation of 10 mcg Sufentanil Tablets Stored at 25° C. and 60% RH in HDPE Bottles or Cartridges With Oxygen Scavengers.

| | "Control" HDPE Bottle | | | | Polycarbonate Lexan HP2 Resin PC-HP2NR-Cartridge | | |
|---|---|---|---|---|---|---|---|
| ~RRT | T = 0 | T = 1 mo | T = 2 mo | T = 3 mo | T = 1 mo | T = 2 mo | T = 3 mo |
| 0.36 | | <QL* | <QL | <QL | <QL | <QL | <QL |
| 0.49/0.5 | 0.28 | <QL | <QL | <QL | 0.25 | 0.15 | 0.12 |
| 0.54/0.55 | 0.11 | <QL | <QL | <QL | 0.11 | <QL | <QL |
| TOTAL | 0.39 | <QL | | | 0.36 | | |

<QL means less than quantitation limit.

TABLE 10B

Stability Evaluation of 10 mcg Sufentanil Tablets Stored at 25° C. and 60% RH in Cartridges With Oxygen Scavengers.

| | | K-Resin-Cartridge | | | PCHP2R-Cartridge | | |
|---|---|---|---|---|---|---|---|
| ~RRT | T = 0 | T = 1 mo | T = 2 mo | T = 3 mo | T = 1 mo | T = 2 mo | T = 3 mo |
| 0.36 | | <QL | <QL | <QL | <QL | <QL | |
| 0.49/0.5 | 0.28 | 0.30 | 0.22 | 0.22 | 0.48 | <QL | <QL |
| 0.54/0.55 | 0.11 | 0.13 | 0.11 | 0.11 | 0.23 | <QL | <QL |
| TOTALS | 0.39 | 0.43 | 0.33 | <QL | 0.71 | <QL | <QL |

Tables 11A and B show the results of HPLC analysis of solid sufentanil dosage forms for the presence of degradation products following storage in HDPE bottles or cartridges made of various materials and containing Stabilox®, at 40° C. and 75% RH, as evidenced by peaks at relative retention times (RRT) of 0.36, 0.49/0.50 and 0.54/0.55 at T=0, 1 month, 2 months and 3 months.

TABLE 11A

Stability Evaluation of 10 mcg Sufentanil Tablets Stored at 40° C. and 75% RH in Cartridges With Oxygen Scavengers.

| | | "Control"-HDPE Bottle | | | PC-HP2NR-Cartridge | | |
|---|---|---|---|---|---|---|---|
| | T = 0 | T = 1 mo | T = 2 mo | T = 3 mo | T = 1 mo | T = 2 mo | T = 3 mo |
| 0.36 | | <QL | <QL | <QL | 0.1 | <QL | 0.11 |
| 0.49/0.5 | 0.28 | <QL | <QL | <QL | <QL | <QL | <QL |
| 0.54/0.55 | 0.11 | 0.13 | 0.2 | 0.15 | <QL | <QL | <QL |
| TOTALS | 0.39 | 0.13 | 0.2 | 0.15 | 0.1 | <QL | 0.11 |

TABLE 11B

Stability Evaluation of 10 mcg Sufentanil Tablets Stored at 40° C. and 75% RH in Cartridges With Oxygen Scavengers.

| | | K-Resin-Cartridge | | | PCHP2R-Cartridge | | |
|---|---|---|---|---|---|---|---|
| | T = 0 | T = 1 mo | T = 2 mo | T = 3 mo | T = 1 mo | T = 2 mo | T = 3 mo |
| 0.36 | | I < QL | <QL | <QL | <QL | <QL | 0.11 |
| 0.49/0.5 | 0.28 | <QL | <QL | <QL | <QL | <QL | <QL |
| 0.54/0.55 | 0.11 | <QL | <QL | <QL | <QL | <QL | <QL |
| TOTALS | 0.39 | <QL | <QL | <QL | <QL | <QL | <QL |

Example 4

Stability Studies with Solid Sufentanil Dosage Forms in Single Dose Applicators (SDAs) in the Presence of Oxygen Scavengers Further studies were carried out on the stability of sufentanil in solid sufentanil dosage forms following storage in SDAs. A study was carried out to evaluate the stability of tablets comprising 10 mcg of sufentanil, having a mass of 5.85 mg following storage in SDAs for 1 month, 2 months and 3 months under different storage conditions in the presence of an oxygen scavenger (Stabilox®).

The storage conditions were the following:
5° C. at ambient humidity;
25° C. and 60% relative humidity (RH); and
40° C. and 75% relative humidity (RH).

The sufentanil formulation is provided in Example 3, above.

The HPLC profile of solid sufentanil dosage forms stored in the presence of oxygen scavengers was evaluated following storage in SDAs for 1 month 2 months, and 3 months, using the conditions provided in Example 1, above.

Tables 12A and B show the results of HPLC analysis of solid sufentanil dosage forms for the presence of degradation products following storage in SDAs and packaging containing oxygen scavengers, at 25° C. and 60% RH, as evidenced by peaks at relative retention times (RRT) of 0.36, 0.49/0.50 and 0.54/0.55 at T=0, 1 month, 2 months and 3 months.

TABLE 12A

Stability Evaluation of 10 mcg Sufentanil Tablets Stored at 2-8° C. and Ambient Humidity in SDAs Packaged With Oxygen Scavengers.

| Time | Individual Unspecified Sufentanil Related Impurities (RS %) | Total (%) |
|---|---|---|
| T = 0 | No Impurity was detected | N/A |
| T = 1 mo | No Impurity was detected | N/A |
| T = 2 mo | No Impurity was detected | N/A |
| T = 3 mo | No Impurity was detected | N/A |

TABLE 12B

Stability Evaluation of 10 mcg Sufentanil Tablets Stored at 25° C. and 60% RH in SDAs Packaged With Oxygen Scavengers.

| Time | Individual Unspecified Sufentanil Related Impurities (RS %) | Total (%) |
| --- | --- | --- |
| T = 0 | No Impurity was detected | N/A |
| T = 1 mo | No Impurity was detected | N/A |
| T = 2 mo | No Impurity was detected | N/A |
| T = 3 mo | No Impurity was detected | N/A |

TABLE 12C

Stability Evaluation of 10 mcg Sufentanil Tablets Stored at 40° C. and 75% RH in SDAs Packaged With Oxygen Scavengers.

| Time | Individual Unspecified Sufentanil Related Impurities (RS %) | Total (%) |
| --- | --- | --- |
| T = 0 | No Impurity was detected | N/A |
| T = 1 mo | No Impurity was detected | N/A |
| T = 2 mo | No Impurity was detected | N/A |
| T = 3 mo | No Impurity was detected | N/A |

What is claimed is:

1. A packaged solid sufentanil drug dosage form comprising:
   (a) a solid sufentanil drug dosage form;
   (b) a primary package containing said solid sufentanil drug dosage form and an oxygen scavenger, wherein the percentage of sufentanil oxidative degradation products is minimized or eliminated in a solid sufentanil drug dosage form packaged with said oxygen scavenger relative to a solid sufentanil drug dosage form packaged in the absence of an oxygen scavenger.

2. The packaged solid sufentanil drug dosage form according to claim 1, wherein the drug dosage form has a mass of less than 30 mg or a volume of less than 30 mcL.

3. The packaged solid sufentanil drug dosage form according to claim 1, wherein the drug dosage form has a mass of less than 10 mg or a volume of less than 10 mcL.

4. The packaged solid sufentanil drug dosage form according to claim 1, wherein the amount of sufentanil in said solid sufentanil drug dosage form is selected from the group consisting of 5 mcg, 10 mcg, 15 mcg, 20 mcg, 30 mcg, 40 mcg, 50 mcg, 60 mcg, 70 mcg, 80 mcg and 100 mcg of sufentanil.

5. The packaged solid sufentanil drug dosage form according to claim 2, wherein the amount of sufentanil in said solid sufentanil drug dosage form is selected from the group consisting of 5 mcg, 10 mcg, 15 mcg, 20 mcg, 30 mcg, 40 mcg, 50 mcg, 60 mcg, 70 mcg, 80 mcg and 100 mcg of sufentanil.

6. The packaged solid sufentanil drug dosage form according to claim 3, wherein the amount of sufentanil in said solid sufentanil drug dosage form is selected from the group consisting of 5 mcg, 10 mcg, 15 mcg, 20 mcg, 30 mcg, 40 mcg, 50 mcg, 60 mcg, 70 mcg, 80 mcg and 100 mcg of sufentanil.

7. The packaged solid sufentanil drug dosage form according to claim 1, wherein said solid sufentanil drug dosage form is stored for at least 6 months under conditions selected from the group consisting of 5° C. and ambient humidity, 25° C. and 60% relative humidity and 40° C. and 75% relative humidity.

8. The packaged solid sufentanil drug dosage form according to claim 5, wherein said solid sufentanil drug dosage form is stored for at least 6 months under conditions selected from the group consisting of 5° C. and ambient humidity, 25° C. and 60% relative humidity and 40° C. and 75% relative humidity.

9. The packaged solid sufentanil drug dosage form according to claim 6, wherein said solid sufentanil drug dosage form is stored for at least 6 months under conditions selected from the group consisting of 5° C. and ambient humidity, 25° C. and 60% relative humidity and 40° C. and 75% relative humidity.

10. The packaged solid sufentanil drug dosage form according to claim 1, further comprising a drug delivery dispenser for housing said solid sufentanil drug dosage form.

11. The packaged solid sufentanil drug dosage form according to claim 10, wherein the drug delivery dispenser is a cartridge.

12. The packaged sufentanil solid sufentanil drug dosage form according to claim 11, wherein the cartridge comprises a desiccant.

13. The packaged solid sufentanil drug dosage form according to claim 10, wherein the drug delivery dispenser is a single dose applicator.

14. The packaged solid sufentanil drug dosage form according to claim 10, wherein the primary package is a foil pouch.

15. The packaged solid sufentanil drug dosage form according to claim 11, wherein the primary package is a foil pouch.

16. The packaged solid sufentanil drug dosage form according to claim 13, wherein the primary package is a foil pouch.

17. The packaged solid sufentanil drug dosage form according to claim 14, wherein oxidative degradation of the sufentanil in said solid sufentanil drug dosage form is not detectable after 6 months of storage at 5° C. and ambient humidity, 25° C. and 60% relative humidity or 40° C. and 75% relative humidity.

18. A method for minimizing or eliminating oxidative degradation of a solid sufentanil drug dosage form comprising:
   (a) providing a solid sufentanil drug dosage form in a drug delivery dispenser;
   (b) further providing an oxygen scavenger;
   (c) placing said drug delivery dispenser and said oxygen scavenger in a primary package made of a substantially oxygen impermeable material, wherein the percentage of sufentanil oxidative degradation products is minimized or eliminated in said solid sufentanil drug dosage form packaged with said oxygen scavenger relative to a solid sufentanil drug dosage form packaged in the absence of an oxygen scavenger.

19. The method according to claim 18, wherein the drug dosage form has a mass of less than 30 mg or a volume of less than 30 mcL.

20. The method according to claim 18, wherein the drug dosage form has a mass of less than 10 mg or a volume of less than 10 mcL.

21. The method according to claim 18, wherein the amount of sufentanil in said solid sufentanil drug dosage form is selected from the group consisting of 5 mcg, 10 mcg, 15 mcg, 20 mcg, 30 mcg, 40 mcg, 50 mcg, 60 mcg, 70 mcg, 80 mcg and 100 mcg of sufentanil.

22. The method according to claim 18, wherein the solid sufentanil drug dosage form is stored for at least 6 months under conditions selected from the group consisting of 5° C. and ambient humidity, 25° C. and 60% relative humidity and 40° C. and 75% relative humidity.

23. The method according to claim 18, wherein said drug delivery dispenser is a cartridge.

24. The method according to claim 23, wherein the cartridge comprises a desiccant.

25. The method according to claim 18, wherein the drug delivery dispenser is a single dose applicator.

26. The method according to claim 18, wherein the primary package is a foil pouch.

* * * * *